United States Patent
Gifford, III et al.

(10) Patent No.: US 12,280,227 B2
(45) Date of Patent: Apr. 22, 2025

(54) VASCULAR TREATMENT DEVICES AND ASSOCIATED SYSTEMS AND METHODS OF USE

(71) Applicant: The Foundry, LLC, Menlo Park, CA (US)

(72) Inventors: Hanson S. Gifford, III, Woodside, CA (US); Edward DeWitt Gifford, Glastonbury, CT (US); Vrad W. Levering, Smithville, TX (US)

(73) Assignee: The Foundry, LLC, Menlo Park, CA (US)

( * ) Notice: Subject to any disclaimer, the term of this patent is extended or adjusted under 35 U.S.C. 154(b) by 819 days.

(21) Appl. No.: 17/250,607

(22) PCT Filed: Aug. 9, 2019

(86) PCT No.: PCT/US2019/046070
§ 371 (c)(1),
(2) Date: Feb. 10, 2021

(87) PCT Pub. No.: WO2020/033933
PCT Pub. Date: Feb. 13, 2020

(65) Prior Publication Data
US 2021/0308433 A1   Oct. 7, 2021

Related U.S. Application Data

(60) Provisional application No. 62/717,752, filed on Aug. 10, 2018.

(51) Int. Cl.
*A61M 25/10* (2013.01)

(52) U.S. Cl.
CPC ... *A61M 25/104* (2013.01); *A61M 2025/1095* (2013.01)

(58) Field of Classification Search
CPC ........ A61M 25/104; A61M 2025/1095; A61M 25/1038
See application file for complete search history.

(56) References Cited

U.S. PATENT DOCUMENTS

| 5,344,402 A | 9/1994 | Crocker |
| 5,470,314 A | 11/1995 | Walinsky |

(Continued)

FOREIGN PATENT DOCUMENTS

| CN | 1434690 A | 8/2003 |
| CN | 102256659 A | 11/2011 |

(Continued)

OTHER PUBLICATIONS

International Search Report and Written Opinion mailed Nov. 28, 2019; International Application No. PCT/US2019/046070; 11 pages.

(Continued)

*Primary Examiner* — Erin McGrath
(74) *Attorney, Agent, or Firm* — Fortem IP LLP

(57) ABSTRACT

Devices, systems, and methods for treating a blood flow passage are discloses herein. In one example, a treatment device includes an expandable element configured to be positioned within the passage and a reinforcing element. The expandable element may have an expanded configuration in which the expandable element defines a lumen therethrough. The reinforcing element may be positioned within the lumen of the expandable element. The reinforcing element may be coupled to the expandable element such that expansion of the expandable element causes the reinforcing element to radially expand, thereby creating a perfusion lumen through the device.

28 Claims, 11 Drawing Sheets

(56) References Cited

U.S. PATENT DOCUMENTS

| | | | |
|---|---|---|---|
| 5,718,684 | A | 2/1998 | Gupta |
| 6,450,988 | B1 | 9/2002 | Bradshaw |
| 6,494,862 | B1* | 12/2002 | Ray ................... A61M 25/0084 604/264 |
| 7,201,770 | B2 | 4/2007 | Johnson et al. |
| 7,972,351 | B2 | 7/2011 | Trinidad |
| 8,088,100 | B2 | 1/2012 | Blix |
| 8,323,242 | B2 | 12/2012 | Beckham |
| 8,481,139 | B2 | 7/2013 | Horn et al. |
| 2003/0040712 | A1 | 2/2003 | Ray et al. |
| 2003/0060895 | A1 | 3/2003 | French et al. |
| 2004/0019322 | A1 | 1/2004 | Hoffmann |
| 2008/0255506 | A1 | 10/2008 | Wilson |
| 2009/0171284 | A1 | 7/2009 | Burke et al. |
| 2011/0172697 | A1 | 7/2011 | Joensson |
| 2011/0264039 | A1 | 10/2011 | Thielen et al. |
| 2012/0059401 | A1* | 3/2012 | Konstantino ........... A61F 2/958 606/159 |
| 2012/0209375 | A1 | 8/2012 | Madrid et al. |
| 2012/0226303 | A1 | 9/2012 | Roche et al. |
| 2012/0226340 | A1 | 9/2012 | Leschinsky |
| 2015/0313732 | A1 | 11/2015 | Fulton, III |
| 2016/0175565 | A1* | 6/2016 | Schaffer ............ A61M 25/1002 606/194 |
| 2017/0252542 | A1* | 9/2017 | Iwano ................... A61M 25/00 |
| 2017/0252543 | A1 | 9/2017 | Gomes et al. |
| 2017/0252544 | A1 | 9/2017 | Gomes et al. |
| 2018/0153692 | A1 | 6/2018 | Gerhardt et al. |
| 2019/0053928 | A1 | 2/2019 | Geldenhuys et al. |
| 2023/0041152 | A1 | 2/2023 | Gifford et al. |

FOREIGN PATENT DOCUMENTS

| | | |
|---|---|---|
| CN | 103476349 A | 12/2013 |
| CN | 106794332 A | 5/2017 |
| CN | 107896485 A | 4/2018 |
| EP | 4103256 A1 | 12/2022 |
| WO | 9615825 A1 | 5/1996 |
| WO | 2010029190 A1 | 3/2010 |
| WO | 2012099979 A1 | 7/2012 |
| WO | 2017189888 A1 | 11/2017 |
| WO | 2021163635 A1 | 8/2021 |

OTHER PUBLICATIONS

Keenan et al., Design of an everting balloon to deploy a microendoscope to the fallopian tubes, Proc. SPIE 9689, Photonic Therapeutics and Diagnostics XII, 968944 (Mar. 8, 2016), 7 pages.

* cited by examiner

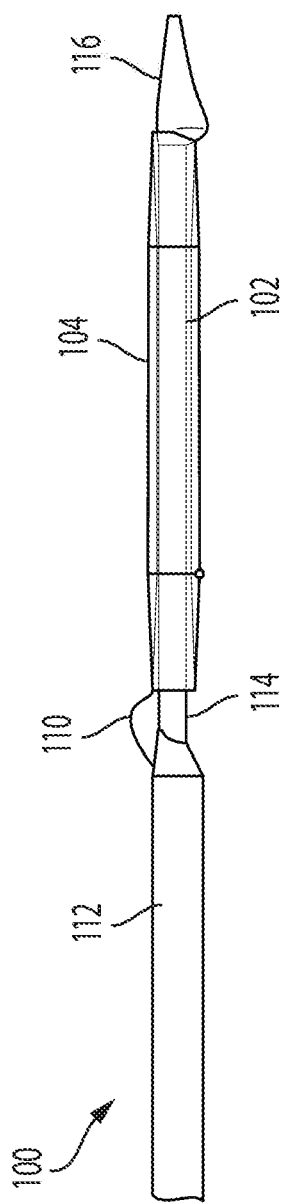
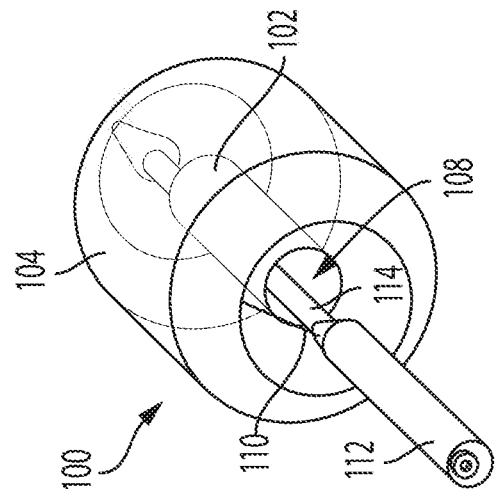
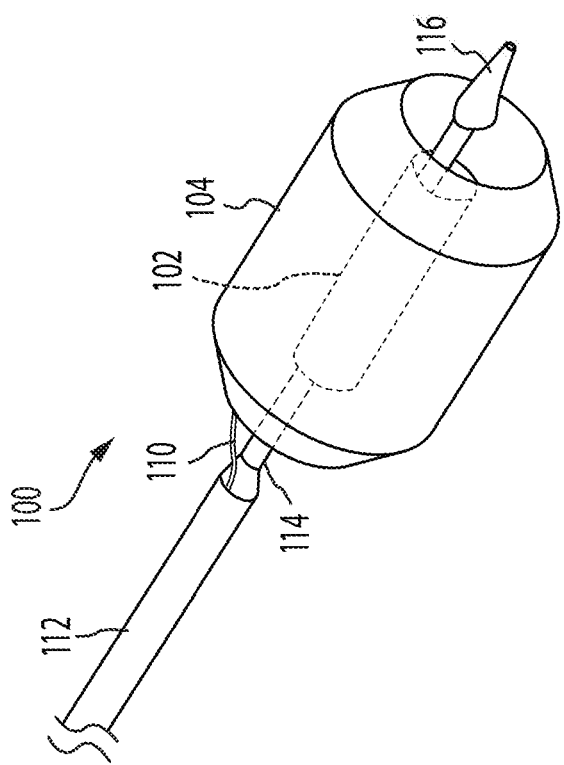
FIG. 2A
FIG. 2C
FIG. 2B

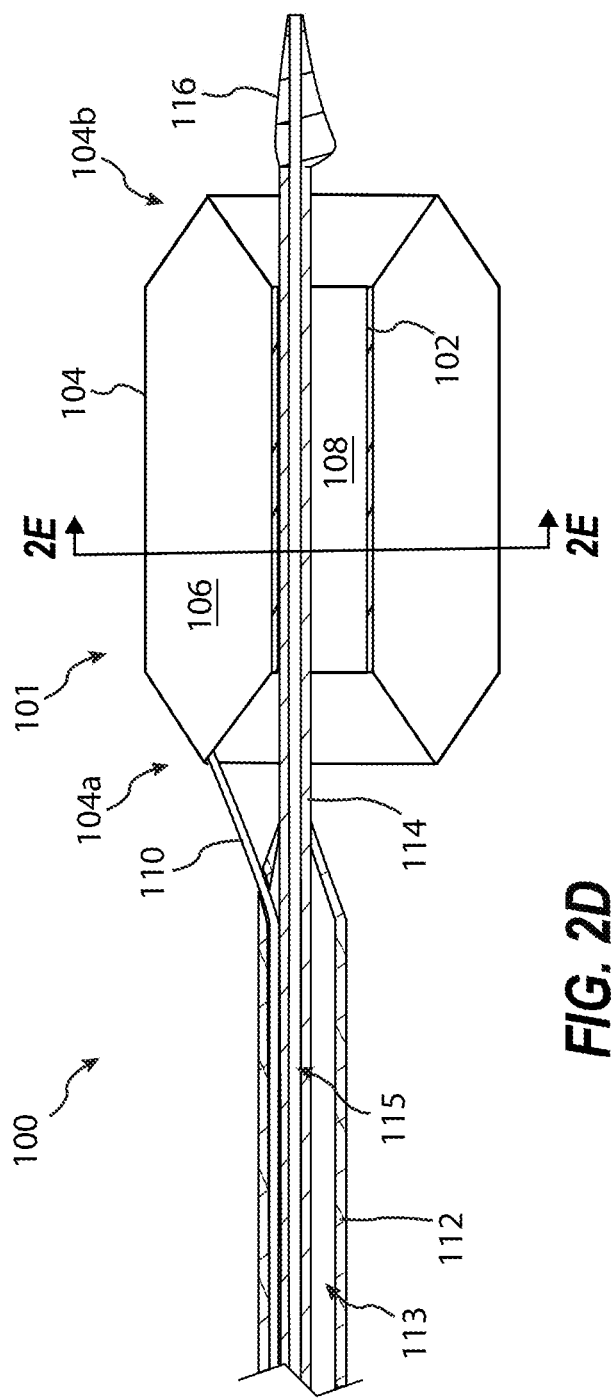
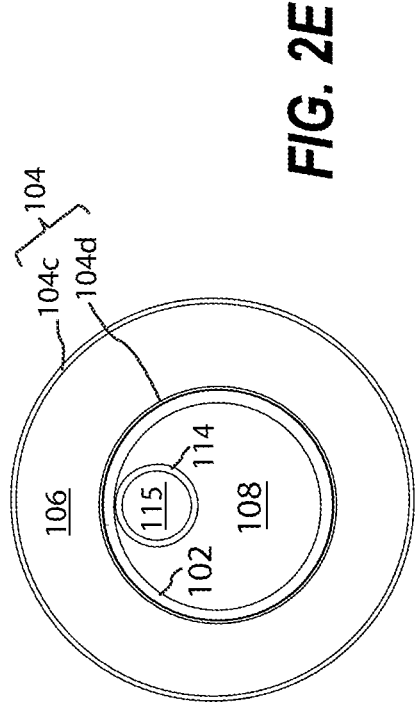
FIG. 2D
FIG. 2E

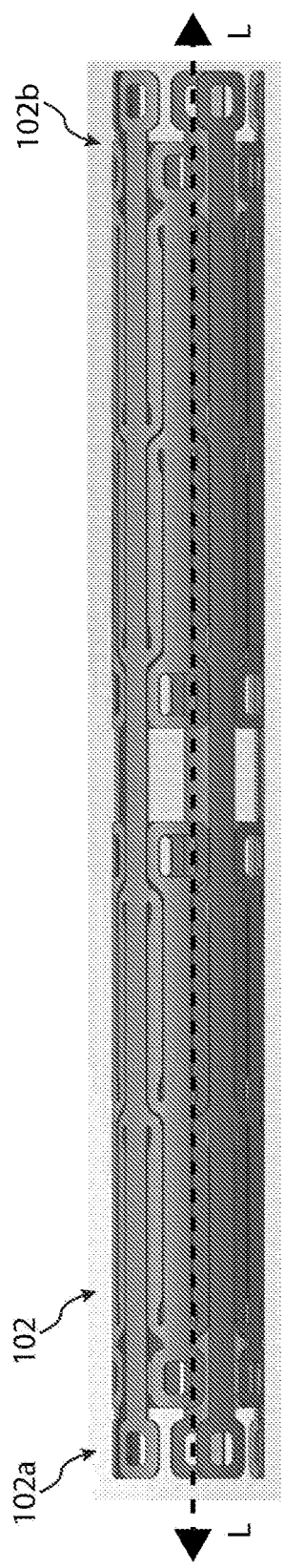
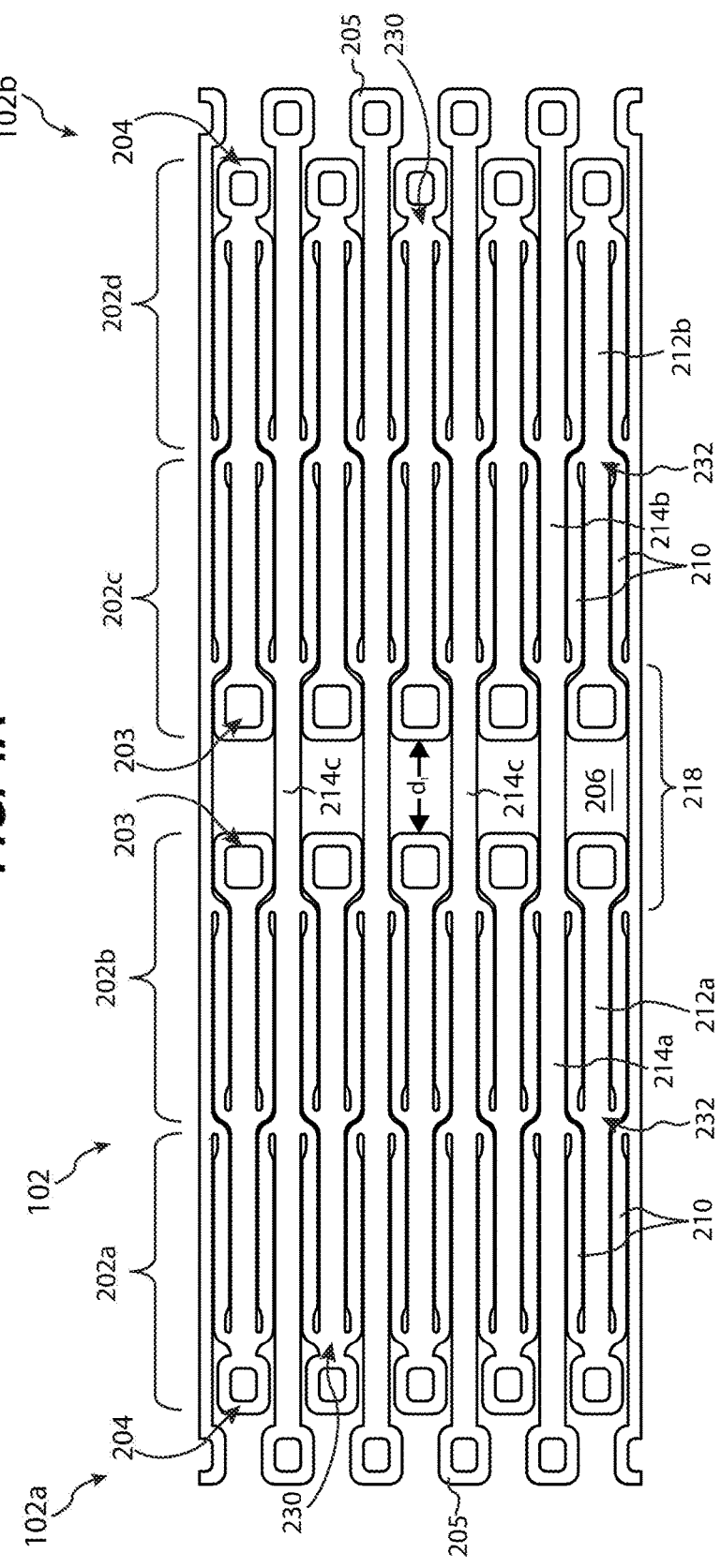
FIG. 4A
FIG. 4B

VASCULAR TREATMENT DEVICES AND ASSOCIATED SYSTEMS AND METHODS OF USE

CROSS-REFERENCE TO RELATED APPLICATIONS

This application is a 371 U.S. national phase application of International Application No PCT/US2019/046070, filed Aug. 9, 2019, which claims the benefit of priority to U.S. Provisional Application No. 62/717,752, filed Aug. 10, 2018, which are hereby incorporated by reference in their entireties.

TECHNICAL FIELD

The present technology is directed to treatment devices, systems, and methods for treating cardiac disease. In particular, the present technology relates to devices for treating blood vessels and associated systems and methods of use.

BACKGROUND

There are many situations in interventional vascular procedures where there is a need to inflate a balloon in a vessel while maintaining perfusion through that vessel. For example, when delivering a balloon-expandable stent in a coronary artery, it is preferable to maintain blood flow through the artery to avoid ischemic damage to the myocardium perfused by that artery. One device commonly used to maintain blood flow is a perfusion balloon catheter. These catheters typically have a relatively large central guidewire lumen with holes through the catheter sidewall into the lumen just proximal to the balloon. This allows blood to flow through the side holes, into the guidewire lumen, and out the distal end of the catheter to maintain perfusion when the balloon is inflated and occluding the vessel.

However, these perfusion balloons are typically only used in smaller vessels where a relatively small perfusion lumen is sufficient, and the catheter can be made with a perfusion lumen of a fixed size, for example a lumen of less than 2 mm in diameter. In larger vessels such as the aorta, maintaining adequate distal perfusion without a high pressure gradient through the perfusion lumen requires a much larger lumen.

Two common interventional procedures that utilize balloon expansion are (a) balloon valvuloplasty of the aortic valve, and (b) catheter-based delivery of balloon-expandable replacement aortic valves (commonly referred to as "transcatheter aortic valve replacement" or "TAVR"). FIG. 1 shows the delivery of a replacement aortic valve on a conventional balloon catheter. Conventional practice is to inflate the balloon to a large diameter (about 20-30 mm) at a very high pressure, blocking all flow to the systemic circulation. It also prevents any blood from leaving the left ventricle, which can lead to a dangerous acute expansion of the ventricle. In order to prevent this dangerous expansion of the ventricle, a temporary pacing catheter is placed in the heart and the heart is typically paced at a very high rate (~200 beats per minute) which prevents it from filling between heartbeats. Such rapid ventricular pacing may cause myocardial ischemia, malignant arrhythmias, low output, reduced cerebral oxygen saturation, and/or increased procedure time and risk of stroke. To avoid or reduce the likelihood of these dangers, the valvuloplasty or TAVR balloon is typically inflated for less than a minute.

In a typical balloon catheter, the balloon is formed from a single extrusion which is expanded into the desired balloon shape and welded or bonded to the shaft of a catheter. The sidewall of the catheter is cut to create an opening to connect an inflation lumen running through the catheter shaft to the interior of the balloon. In most clinical applications in which a vessel or valve is being dilated, the outer surface of the balloon is rounded (i.e., has a functionally circular cross-sectional shape) so as to apply a relatively even radial force against the apposing tissue. It is difficult to locate a perfusion lumen at the outer circumference of the balloon while maintaining this rounded/circular shape and providing even radially outward force.

An existing approach to the foregoing challenge of creating a large perfusion lumen in larger balloon catheters is the TRUE® Flow Valvuloplasty Perfusion Catheter (C. R. Bard/Becton Dickenson). The TRUE® Flow device has several smaller balloons arranged around the periphery of a central lumen and surrounded by a fiber-based shell. When inflated, the balloons hold the central lumen open. However, this approach limits the effective pressure which can be applied to the circumference of the balloon, even when these smaller balloons are inflated to a higher pressure. More importantly, the use of multiple balloons employs a large amount of material which increases a deflated diameter of the device and makes delivery of the device through a delivery sheath more difficult. This is especially true in the case of a TAVR balloon that has the additional bulk of the prosthetic valve.

Therefore, there remains a need for improved balloons for interventional procedures, especially within the field of interventional cardiology.

SUMMARY

The subject technology is illustrated, for example, according to various aspects described below, including with reference to FIGS. 2A-10B. Various examples of aspects of the subject technology are described as numbered clauses (1, 2, 3, etc.) for convenience. These are provided as examples and do not limit the subject technology.

1. A device for treating a blood flow passage of a patient, the device comprising:
   an expandable element configured to be positioned within the passage, the expandable element having a collapsed configuration and an expanded configuration in which the expandable element defines a lumen therethrough; and
   a reinforcing element positioned within the lumen of the expandable element, the reinforcing element having a collapsed configuration and an expanded configuration in which the reinforcing element defines a lumen therethrough, wherein the reinforcing element is coupled to the expandable element such that expansion of the expandable element causes the reinforcing element to radially expand, thereby creating a perfusion lumen through the device.

2. A device for treating cardiac or cardiovascular disease, the device comprising:
   an expandable element comprising an outer wall and an inner wall, the outer and inner walls meeting at their respective longitudinal ends, wherein the expandable element has a collapsed configuration and an expanded configuration, and wherein the inner wall defines a lumen extending along a longitudinal axis of the expandable element; and
   a reinforcing element positioned within the lumen, wherein expansion of the expandable element from a collapsed configuration to an expanded configuration causes the reinforcing element to radially expand.

3. The device of Clause 1 or Clause 2, wherein the device is configured such that expansion of the expandable element while the device is positioned within the passage urges the reinforcing element towards its expanded configuration, thereby allowing blood flow through the lumen of the reinforcing element and the lumen of the expandable element while the expandable element is in the expanded configuration.

4. The device of any one of the preceding Clauses, wherein the device is configured such that expansion of the expandable element while the device is positioned within the passage pulls the reinforcing element towards its expanded configuration, thereby allowing blood flow through the lumen of the reinforcing element and the lumen of the expandable element while the expandable element is in the expanded configuration.

5. The device of any one of the preceding Clauses, wherein the expandable element causes radial expansion of the reinforcing element by applying a longitudinally oriented force to the reinforcing element.

6. The device of Clause 5, wherein the force is longitudinally extensive.

7. The device of Clause 5, wherein the force is longitudinally compressive.

8. The device of any one of the preceding Clauses, wherein the expandable element causes radial expansion of the reinforcing element by applying a radially oriented force along the reinforcing element.

9. The device of Clause 8, wherein the force is radially extensive.

10. The device of any one of the preceding Clauses, wherein the reinforcing element is mechanically coupled to the expandable element during delivery of the device through a sheath to a treatment site.

11. The device of any one of the preceding Clauses, wherein the reinforcing element is mechanically coupled to the expandable element at all times.

12. The device of any one of the preceding Clauses, wherein expansion of the expandable element causes substantially simultaneous radial expansion of the reinforcing element to its expanded configuration.

13. The device of any one of the preceding Clauses, wherein the expandable element is an inflatable element configured to expand when an inflation fluid is delivered to an interior region of the inflatable element.

14. The device of any one of the preceding Clauses, wherein the expandable element extends between first and second longitudinal ends, and wherein the expandable element comprises a fold at the first longitudinal end and a seam at the second longitudinal end.

15. The device of any one of the preceding Clauses, wherein the expandable element defines a single, continuous inflation cavity.

16. The device of any one of the preceding Clauses, wherein the expandable element defines a single, continuous, annular inflation cavity.

17. The device of any one of the preceding Clauses, wherein the expandable element is a balloon.

18. The device of any one of the preceding Clauses, wherein the expandable element has a toroidal shape in the expanded configuration.

19. The device of any one of the preceding Clauses, wherein the expandable element has an elongated toroidal shape in the expanded configuration.

20. The device of any one of the preceding Clauses, wherein the expandable element is configured to be inflated to a pressure of at least about 30 to about 105 psi (about 2 to about 7 atmospheres).

21. The device of any one of the preceding Clauses, wherein the expandable element is configured to be inflated to an internal pressure sufficient to effectively dilate stenosed native valves and/or aortic strictures.

22. The device of any one of the preceding Clauses, wherein a diameter of the perfusion lumen when the device is in an expanded state is sufficient to reduce any pressure gradient of blood flowing through the perfusion lumen.

23. The device of any one of the preceding Clauses, wherein a diameter of the perfusion lumen when the device is in an expanded state is sufficient to minimize any pressure gradient of blood flowing through the perfusion lumen.

24. The device of any one of the preceding Clauses, wherein a diameter of the perfusion lumen is at least one-third of a diameter of the blood flow passage.

25. The device of any one of the preceding Clauses, wherein expansion of the expandable element creates a perfusion lumen through the expandable element and the reinforcing element, and wherein the perfusion lumen is configured to remain open while the expandable element is in the expanded configuration.

26. The device of any one of the preceding Clauses, wherein the device is configured such that foreshortening of the expandable element urges the reinforcing element to radially expand, thereby increasing a diameter of the lumen of the reinforcing element.

27 The device of any one of the preceding Clauses, wherein the reinforcing element is a mesh.

28 The device of any one of the preceding Clauses, wherein the reinforcing element is a braid.

29 The device of any one of the preceding Clauses, wherein the reinforcing element is a coil.

30. The device of any one of the preceding Clauses, wherein the reinforcing element is a laser-cut stent.

31. The device of any one of the preceding Clauses, further comprising a connector having:
  a first portion coupled to the reinforcing element at a first location;
  a second portion coupled to the reinforcing element at a second location; and
  an intermediate portion between the first and second portions, wherein the intermediate portion extends over a radially outer surface of the expandable element.

32. The device of Clause 31, wherein the intermediate portion of the connector extends substantially longitudinally along the radially outer surface of the expandable element.

33. The device of Clause 31, wherein the connector comprises at least one of a strand, a suture, a wire, a thread, a tether, a fiber, or a filament.

34. The device of Clause 31, wherein expansion of the expandable element causes the connector to pull the first and second locations toward one another, thereby causing the reinforcing element to radially expand.

35. The device of Clause 31, wherein expansion of the expandable element causes the connector to pull the first and second locations away from one another, thereby causing the reinforcing element to radially expand.

36. The device of Clause 31, wherein the first location comprises a first eyelet of the reinforcing element and the second location comprises a second eyelet of the reinforcing element.

37. The device of Clause 36, wherein a longitudinal distance between the first and second eyelets decreases in response to expansion of the expandable element.

38. The device of Clause 36, wherein a longitudinal distance between the first and second eyelets increases in response to expansion of the expandable element.

39 The device of any one of Clauses 36 to 38, wherein the first and second eyelets are substantially circumferentially aligned.

40. The device of any one of Clauses 36 to 38, wherein the first and second eyelets are circumferentially offset.

41. The device of any one of Clauses 36 to 40, wherein the first and second eyelets are positioned at opposing longitudinal ends of the reinforcing element.

42. The device of any one of Clauses 36 to 40, wherein both of the first and second eyelets are positioned between the first and second longitudinal ends of the reinforcing element.

43. The device of any one of Clauses 31 to 37, further comprising a plurality of connectors, each having first and second portions coupled to the reinforcing element and an intermediate portion between the first and second portions, the intermediate portion extending over the radially outer surface of the expandable element.

44. The device of Clause 40, wherein the connectors are spaced apart from one another around the radially outer surface of the expandable element.

45. The device of any one of the preceding Clauses, the reinforcing element extending longitudinally between first and second ends and having a first location and a second location, the first location positioned at a longitudinal location along the reinforcing element between the first end and the second location, wherein the device further comprises a connector that extends from the second location past the first location to the first end, then inverts and extends along an outer surface of the expandable element to the second end of the reinforcing element, then inverts and extends along the reinforcing element towards the second end past the second location to the first location.

46. The device of any one of the preceding Clauses, further comprising a travel limiter configured to limit longitudinal elongation and/or compression of the reinforcing element in response to expansion of the expandable element.

47. The device of Clause 46, wherein the travel limiter comprises one or more pairs of opposing eyelets coupled via a flexible connector.

48. The device of Clause 47, wherein a longitudinal distance between opposing eyelets decreases in response to expansion of the expandable element.

49. The device of Clause 47 or 48, wherein the connector prevents the eyelets from longitudinally overlapping or moving past one another.

50. The device of any one of the preceding Clauses, wherein the reinforcing element comprises a plurality of interconnected struts.

51. The device of any one of the preceding Clauses, wherein the reinforcing element includes a first circumferential portion and a second circumferential portion, and wherein (a) a longitudinal length of the first circumferential portion changes as the expandable element expands and contracts, and (b) a longitudinal length of the second circumferential portion remain constant as the expandable element expands and contracts.

52. The device of any one of the preceding Clauses, wherein the reinforcing element is coupled to the expandable element via a flexible connector.

53. The device of any one of the preceding Clauses, wherein at least a portion of an outer surface of the reinforcing element is adhered to at least a portion of the outer surface of the inner wall of the expandable element.

54. The device of any one of the preceding Clauses, wherein the ends of the reinforcing element are directly attached to the ends of the expandable element such that expansion of the expandable element causes either lengthening or foreshortening of the expandable element, thereby causing expansion of the reinforcing element.

55. The device of any one of the preceding Clauses, wherein a length of the reinforcing element is less than a length of the expandable element.

56. The device of any one of the preceding Clauses, wherein a length of the reinforcing element is different than a length of the expandable element.

57. The device of any one of the preceding Clauses, wherein a length of the reinforcing element is greater than a length of the expandable element.

58. The device of any one of the preceding Clauses, wherein an entire length of the reinforcing element is positioned within the lumen of the expandable element.

59. The device of any one of the preceding Clauses, wherein a portion of the length of the reinforcing element extends proximally beyond a proximal end of the expandable element, distally beyond a distal end of the expandable element, or both.

60. The device of any one of the preceding Clauses, further comprising a valve coupled to the reinforcing element and/or the expandable element, wherein the valve is configured to control fluid flow through the lumen of the reinforcing element.

61. The device of Clause 60, wherein the valve is a one-way valve.

62 The device of Clause 60 or 61, wherein the valve is one of an iris valve, a multi-leaflet valve, a duckbill valve, or a windsock valve.

63. The device of any one of the preceding Clauses, further comprising an expandable implantable valve apparatus positioned around an outer surface of the expandable element.

64. The device of Clause 63, wherein the expandable implantable valve apparatus comprises a laser-cut stent and a prosthetic heart valve configured for implantation at a native valve annulus.

65. The device of any one of the preceding Clauses, wherein the passage is a native valve annulus.

66. The device of any one of the preceding Clauses, wherein the passage is a native heart valve annulus.

67. The device of any one of the preceding Clauses, wherein the passage is an aortic valve annulus.

68. The device of any one of the preceding Clauses, wherein the passage is a blood vessel.

69. A system for treating a blood flow passage of a patient, the system comprising:
  a treatment element comprising any of the devices of Clauses 1-68;
  a first elongated member defining a lumen therethrough, the lumen in fluid communication with an interior region of the expandable element, wherein the first elongated member is configured to deliver a fluid to an interior region of the expandable element to expand the expandable element; and
  a second elongated member, wherein a distal portion of the second elongated member is coupled to the reinforcing element.

70. The system of any one of the preceding Clauses, wherein the second elongated member defines a lumen extending therethrough, and wherein the lumen is configured to slidably receive a guidewire.

71. The system of any one of the preceding Clauses, wherein only a portion of the reinforcing element is fixed to the second elongated member such that the reinforcing element can change in length while coupled to the second elongated member.

72. The system of any one of the preceding Clauses, further comprising a third elongated member configured to receive the first elongated member and the second elongated member therethrough.

73. The system of Clause 72, wherein the third elongated member terminates distally at a location proximal of the expandable element.

74. The system of any one of the preceding Clauses, further comprising an atraumatic distal tip at a distal end of the second elongated member.

75. A method for treating a blood flow passage of a patient with any of the treatment devices, treatment systems, or treatment elements of the preceding Clauses.

76. A method for treating a blood flow passage of a patient, the method comprising:
delivering a treatment element in a collapsed configuration to a treatment site within the blood flow passage, the treatment element comprising an expandable element and a reinforcing element positioned at least partially within a lumen of the expandable element; and
creating a perfusion lumen by radially expanding the expandable element at the treatment site, wherein the perfusion lumen extends through the treatment element while the expandable element is in an expanded configuration.

77. The method of any one of the preceding Clauses, wherein radial expansion of the expandable element causes radial expansion of the reinforcing element.

78. The method of any one of the preceding Clauses, wherein radial expansion of the expandable element exerts a longitudinally compressive force on the reinforcing element, thereby causing the reinforcing element to radially expand within the lumen of the expandable element.

79. The method of any one of the preceding Clauses, wherein the reinforcing element has first and second locations spaced apart along its longitudinal axis, and wherein radial expansion of the expandable element pulls the first and second locations in longitudinally opposing directions.

80. The method of any one of the preceding Clauses, wherein expansion of the expandable element radially expands the reinforcing element, and wherein the perfusion lumen extends through a lumen of the expanded reinforcing element.

81. The method of any one of the preceding Clauses, wherein expanding the expandable element comprises delivering an inflation fluid to an interior region of the expandable element.

82. The method of any one of the preceding Clauses, wherein the expandable element is a balloon.

83. The method of any one of the preceding Clauses, wherein expansion of the expandable element while the device is positioned within the blood flow passage pulls the reinforcing element towards its expanded configuration.

84. The method of any one of the preceding Clauses, further comprising exerting a radially outward force against a radially inner surface of the expandable element with the reinforcing element.

85. The method of any one of the preceding Clauses, wherein the treatment element is any of the treatment devices and/or treatment elements of the preceding Clauses.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2A is a side view of a distal portion of a treatment system of the present technology, shown in a collapsed state.

FIGS. 2B and 2C are front and rear isometric views, respectively, of a distal portion of the treatment system of the present technology, shown in an expanded state.

FIG. 2D is a cross-sectional side view of the treatment system of the present technology in an expanded state.

FIG. 2E is a cross-sectional end view of the treatment system of the present technology taken along line 2E-2E in FIG. 2D.

FIG. 4A is a side view of a reinforcing element of the present technology in a rolled-up, collapsed state.

FIG. 4B is a top view of a reinforcing element of the present technology in a laid-flat configuration.

DETAILED DESCRIPTION

Figure 1:
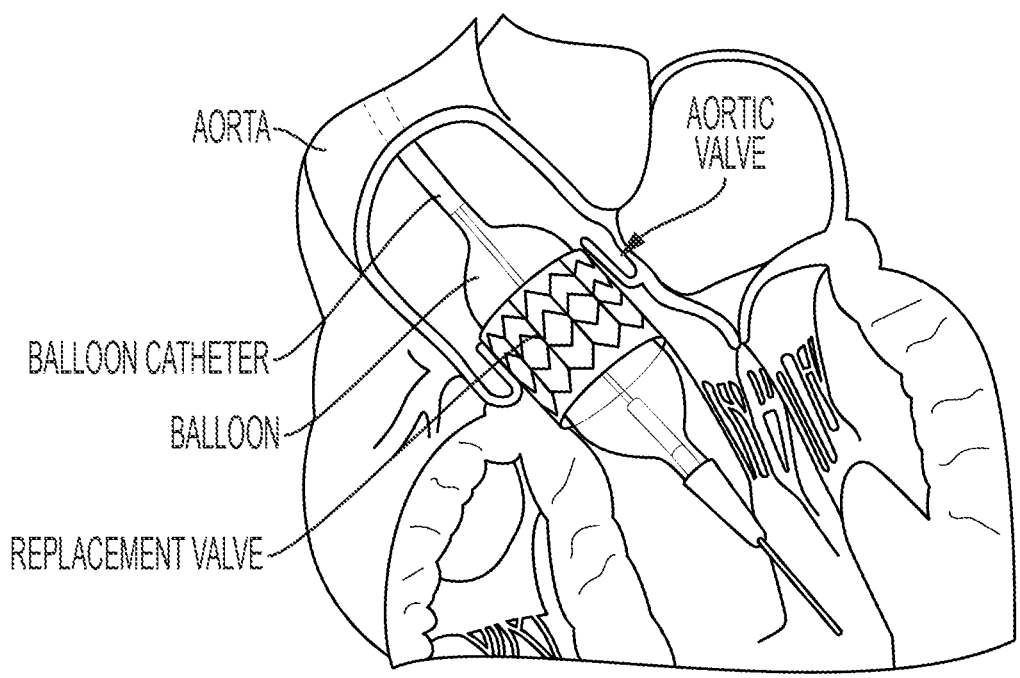
FIG. 1 depicts a conventional balloon catheter and replacement valve positioned at the aortic valve during a typical TAVR procedure.

Specific details of several embodiments of the technology are described below with reference to FIGS. 2A-10B. Although many of the embodiments are described below with respect to devices, systems, and methods for percutaneous replacement of a native aortic valve, other applications and other embodiments in addition to those described herein are within the scope of the technology, such as devices, systems, and methods for performing a balloon valvuloplasty, for dilating aortic strictures or other narrowings in the circulatory system, and devices, systems, and methods for percutaneous replacement of a native mitral valve, a native tricuspid valve, and/or a native pulmonic valve. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 2A-10B.

With regard to the terms "distal" and "proximal" within this description, unless otherwise specified, the terms can reference a relative position of the portions of an interventional device such as a prosthetic valve device and/or an associated delivery device with reference to an operator and/or a location in the vasculature or heart. For example, in referring to a delivery system including the perfusion devices described herein, "proximal" can refer to a position closer to the operator of the device or an incision into the vasculature, and "distal" can refer to a position that is more distant from the operator of the device or further from the incision along the vasculature (e.g., the end of the catheter).

FIG. 2A is a side view of a distal portion of a treatment system 100 of the present technology, shown with a treatment element 101 in a collapsed state. FIGS. 2B and 2C are front and rear isometric views, respectively, of the distal portion of the treatment system 100 with the treatment element 101 in an expanded state. As used herein with reference to the treatment system 100, "expanded configuration" and "collapsed configuration" refer to the configuration of the treatment system 100 when the treatment element 101 is expanded or collapsed, respectively. Likewise, the use of "deployed" with respect to the treatment element 101 or treatment system 100 refers to a configuration in which the treatment element 101 is in a fully or partially expanded configuration.

The treatment system 100 is configured to position and deploy the treatment element 101 at a treatment site within a blood flow passage of a patient to provide a perfusion lumen while the expandable element 104 is deployed during an interventional procedure. As used herein, "blood flow passage" refers to any anatomical structure through which blood regularly flows. Examples of blood flow passages include a native annulus (in the heart or anywhere in the vasculature), a heart chamber, a blood vessel, and other body lumens. The treatment element 101 may be delivered in the collapsed state through a guide catheter to the treatment site within the blood flow passage. When treating a blood flow passage at or within the heart, the treatment system 100 may deliver the treatment element 100 to the heart via transfemoral, transcaval, trans-aortic, trans-venous, trans-atrial, transaxilliary/subclavian, or trans-apical approaches, antegrade or retrograde to the direction of blood flow, and may include trans-septal crossing from the right atrium to the left atrium.

The treatment systems 100 of the present technology may be used in any medical procedure that employs balloon expansion within a blood flow passage, regardless of whether the balloon (or other expandable element) is expanded directly into contact with the surrounding passage tissue or indirectly with another structure positioned between the balloon and the passage tissue (such as a stent, stent-graft, or prosthetic heart valve apparatus). The treatment systems 100 disclosed herein, for example, provide a reinforced perfusion lumen through a balloon while the balloon is expanded within a native valve annulus to widen the native valve opening during a valvuloplasty or to position a prosthetic valve during a TAVR procedure. The treatment systems 100 of the present technology may be used for delivery of repair or replacement devices to any of the four major cardiac valves (aortic, mitral, tricuspid, and pulmonic), as well as dilation of strictures or stents in the aorta or any of the great vessels or other blood vessels, and others. It might also be used for temporary sealing of aortic ruptures, uncontrolled bleeding sites, aortic dissections, or other areas where sealing of the vessel while sustaining perfusion is desired. Additionally, the treatment systems 100 of the present technology may be utilized in trans-septal as well as fenestrated aortic applications, where target vessel or lesion access requires navigation through tortuous anatomy. In such scenarios, a outer, large diameter balloon (such as the expandable element of the present technology) allows for fixation adjacent to the target lesion or vessel. In some cases, treatment systems for additional stent or balloon dilation could be delivered through the central lumen of the expandable element of the present technology.

As shown in FIGS. 2A-2C and the cross-sectional views of FIGS. 2D and 2E, the treatment system 100 may comprise the treatment element 101 and one or more elongated members configured to carry or otherwise functionally support the treatment element 101 within the blood flow passage. The treatment element 101 comprises an inner reinforcing element 102 (e.g., a stent) and an outer expandable element 104 (e.g., a balloon) positioned around the reinforcing element 102. As described in greater detail below, the reinforcing element 102 is coupled to the expandable element 104 such that inflation of the expandable element 104 causes radial expansion of the reinforcing element 102, thereby creating a perfusion lumen 108 through the deployed treatment element 101 at the treatment site that allows blood to flow through the passage while the expandable element 104 is deployed during the interventional procedure. If the expandable element 104 were to be inflated (or otherwise expanded) without deploying the inner reinforcing element 102, the pressure in the expandable element 104 may collapse the perfusion lumen 108. As such, the reinforcing element 102 provides a radially outward force against an inner surface of the expandable element 104 to maintain a perfusion lumen through the expandable element 104 while it is inflated.

In some embodiments, the expandable element 104 comprises an inflatable element, such as a balloon. The expandable element 104 can comprise one or more substantially fluid-impermeable materials commonly used for balloons used in interventional procedures, such as polyethylene, polyolefin, polyurethane, nylon (polyamide), polyethylene terephthalate (PET or polyester), and/or other suitable polymers. In several examples of the technology, the expandable element 104 may comprise a composite structure formed of one or more polymer(s) and reinforcing fibers, such as Kevlar, carbon-fiber, spectra or other high molecular weight polyethylenes, or other fibers in any orientation.

As best shown in the cross-sectional view of FIG. 2E, the expandable element 104 may comprise an elongated, annular balloon formed of an outer wall 104c and an inner wall 104d that together enclose an interior region 106. The interior region 106 may be configured to receive a fluid to inflate or otherwise expand the expandable element 104. The outer and inner walls 104c and 104d of the expandable element 104 may be substantially impermeable to fluid such that delivery of a fluid to the interior region 106 when the expandable element 104 is in its collapsed configuration forces the outer wall 104c to move radially away from the inner wall 104d, thereby causing the expandable element 104 to radially expand. It may also become longer, or it may foreshorten with respect to the elongate member as it expands radially. As can be seen in comparing the collapsed configuration of the expandable element 104 (FIG. 2A) to its expanded configuration (FIGS. 2B-2E), the expandable element 104 may be slightly longer in its collapsed configuration than in its expanded configuration.

In some embodiments, such as that shown in FIGS. 2A-2F, the expandable element 104 may be formed of an inverted tube such that the expandable element 104 comprises a seam at a proximal or first longitudinal end 104a (FIG. 2D) and a fold (and no seam) at a distal or second longitudinal end 104b (FIG. 2D). In some embodiments, the expandable element 104 comprises a fold (and no seam) at the proximal or first longitudinal end 104a (FIG. 2D) and a seam at a distal or second longitudinal end 104b (FIG. 2D). In any case, the fold may comprise the inverted portion of the tube, and the seam may comprise where the two longitudinal ends of the tube meet. Depending on the material used for the expandable element 104 (for example, if using polyurethane), the seam may be welded, or it can also be bonded using flexible bonding agents such as UV-curable urethane methacrylates. The inflation shaft (such as the first elongated member 110, described below) can be made of the same or a similar material and welded or bonded into the seam. It may be preferable to reduce or otherwise minimize any seams, joints or welds in the expandable element 104 to reduce the likelihood of having weakened sections of the expandable element 104 that are less capable of withstanding high pressures.

Figure 3A:
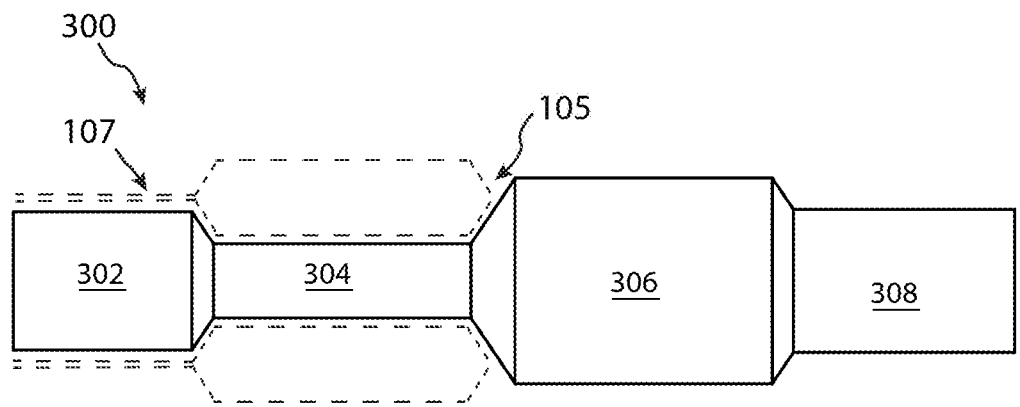
FIGS. 3A and 3B are side and isometric views, respectively, of a mold for forming an expandable element in accordance with the present technology.
Figure 3B:
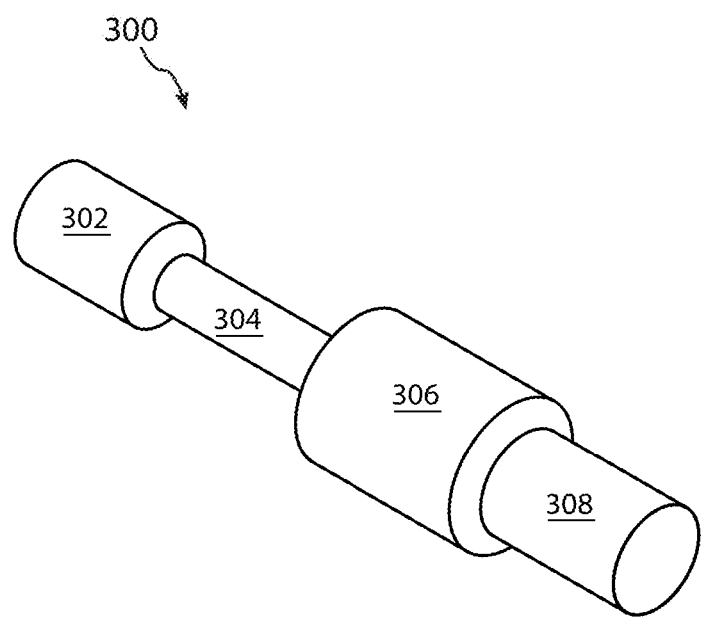

FIGS. 3A and 3B show an example mold 300 for forming an expandable element 104 of the present technology. The mold 300 can have a first portion 302, a second portion 304, a third portion 306, and a fourth portion 308 along its length that result in analogous sections of the resultant balloon. Adjacent portions can have a tapered transition portion therebetween. In some embodiments, a diameter of the second portion 304 may be less than the individual diameters of the first, third, and fourth portions 302, 306, 308, and can reflect the inner diameter of the lumen of the expandable element 104. The dashed line shows an example of a tube that has been placed on the mold, blown to fit the mold shape, and then folded over itself such that the resulting structure has a fold 105 at one end and a seam 107 at the other. A tube (e.g., elongated member 110) can be inserted into the seam 107 to define an inflation lumen. It will be appreciated that the expandable element 104 may have other shapes than that shown in the drawings, and the mold 300 may have other shapes. When in its expanded configuration, the outer wall of the expandable element 104 may have a contour comprised of generally linear sections (as shown in the drawings), or all or certain portions of the expandable element's outer wall may have a more rounded contour than that which is depicted in the drawings.

In some embodiments, the expandable element 104 may comprise a balloon that is everted at both ends so that the two ends overlap along the interior diameter of the balloon. In this configuration, the resulting seam may be disposed at an intermediate portion of the balloon rather than at a proximal or distal end. For example, the seam may be disposed along a central portion of the balloon along the radially inward surface. The two overlapping ends may be bonded together using adhesive, for example. The inflation lumen may be inserted between these two overlapping ends and bonded into the balloon when the ends are bonded together.

In some aspects of the present technology, the expandable element 104 may be constructed using two discrete layers: (a) a first material or layer for the inner wall that may contact the reinforcing element 102 (i.e., facing the lumen 108) and optionally a guidewire shaft (such as the second elongated member 114, detailed below), and (b) one for the outer wall. In some embodiments where the treatment element 101 includes a valve (such as that described with respect to FIGS. 8A and 8B), the outer wall should be connected to the valve so that there is no path for leakage between the expandable element and the valve. The two materials or layers can be bonded at two seams, distal and proximal, with an inflation lumen welded or bonded into the one of the seams.

In some embodiments, the expandable element 104 of the present technology may have one or more of the following features: a very low deflated or collapsed profile to minimize the device diameter on introduction and removal; a relatively large inflated or expanded profile (e.g., about 20 mm to about 30 mm, for example to allow dilation of large valves or vessels such as the aortic valve or the aorta); a large perfusion lumen when inflated or expanded to reduce or minimize any pressure gradient across the expandable element 104 (for example, a diameter of the perfusion lumen 108 when the treatment element 101 is in an expanded state is sufficient to minimize any pressure gradient of blood flowing through the perfusion lumen and/or a diameter of the perfusion lumen is at least one-third of a diameter of the blood flow passage); and capability of withstanding high inflation pressures (e.g., at least about 30 to about 105 psi (about 2 to about 7 atmospheres)) to effectively dilate stenosed valves or aortic strictures.

The expandable element 104 of the present technology provides several advantages over conventional balloon-expandable systems. For example, unlike conventional devices, the expandable element 104 is not formed of a sidewall bonded to a fixed-diameter catheter shaft. Rather, the expandable element 104 has an elongated, annular or toroidal shape with an exterior surface that has both a luminal-facing (e.g., radially inward-facing) portion and a radially outward-facing portion. Moreover, the elongated, annular expandable element 104 of the present technology has a shorter length without necessitating a steeper transition angle from the large diameter since much of the transition is "reversed" by the eversion. The shorter expandable element 104 improves pushability and maneuverability of the treatment system 100 when navigating the more tortuous anatomy.

Referring still to FIGS. 2A-2E, in addition to the treatment element 101, the treatment system 100 may comprise one or more elongated members. For example, the treatment system 100 may comprise a first elongated member 110 defining a first lumen therethrough (not visible in the drawings), a second elongated member 114 defining a second lumen 115 therethrough, which might be used to deliver a guidewire in advance of the rest of the system, and a third elongated member 112 defining a third lumen 113 therethrough. The first elongated member 110 may extend between a proximal end portion (not shown) and a distal end portion that is fluidically coupled to the interior region 106 of the expandable element 104. For example, a distal end portion of the first elongated member 110 may be inserted into and/or placed into fluid communication with the interior region 106 of the expandable element 104 via a seam between the outer and inner walls 104c, 104d (FIG. 2E) at a proximal end portion of the treatment element 101. The first elongated member 110 may be configured to deliver a fluid (e.g., water, saline, a radiopaque solution, air) to the expandable element 104 to expand the expandable element 104.

The second elongated member 114 may extend between a proximal end portion (not shown) and a distal end portion located at or near the treatment element 101. The second elongated member 114 can be a generally tubular shaft defining a lumen 115 therethrough. In some embodiments, the second elongated member 114 is configured to slidably receive a guidewire for atraumatic guidance of the catheter to the appropriate location. The second elongated member 114 may extend through the entire length of the perfusion lumen 108 and terminate distal to a distal end of the treatment element 101, the expandable element 104, and/or the reinforcing element 102. In some embodiments, the second elongated member 114 may terminate at a location that is longitudinally aligned with or proximal of a distal end of the treatment element 101, the expandable element 104, and/or the reinforcing element 102. In some embodiments, the second elongated member 114 may have an atraumatic distal tip at its distal end, as shown in FIGS. 2A-2D.

The second elongated member 114 may be coupled to the reinforcing element 102 such that the reinforcing element 102 is free to radially contract and expand and/or longitudinally contract and expand. For example, the second elongated member 114 may be coupled to the reinforcing element 102 at a single longitudinal location that does not hinder expansion and contraction of the reinforcing element. In some embodiments, the second elongated member 114 may be coupled to the reinforcing element 102 at multiple longitudinal locations along the reinforcing element 102, each of which is not subject to foreshortening (as described in greater detail below).

The third elongated member 112 may comprise a generally tubular shaft defining a lumen 113 therethrough. The third elongated member 112 may extend from a proximal portion (not shown) to a distal portion that terminates at a location longitudinal aligned with or proximal of the treatment element 101, the expandable element 104, and/or the reinforcing element 102. In some embodiments, the third elongated member 112 terminates at a location longitudinally aligned with or distal to a proximal end of the treatment element 101, the expandable element 104, and/or the reinforcing element 102. In some embodiments, the third elongated member 112 extends through the entire length of the treatment element 101, the expandable element 104, and/or the reinforcing element 102.

The third elongated member 112 may receive one or more elongated members (including tubular shafts) through its lumen 113. For example, as shown in FIGS. 2A-2E, the first and second elongated members 110 and 114 extend through the lumen 113 of the third elongated member 112. The third elongated member 112 adds column strength to the treatment system 100, thereby improving pushability.

In some embodiments, the treatment system 100 may have more or fewer elongated members or lumens than that depicted in FIGS. 2A-2E.

FIGS. 4A and 4B depict an example reinforcing element 102 for use with the treatment systems 100 of the present technology, shown in tubular and laid flat configurations, respectively. As demonstrated by FIGS. 4A and 4B, in some embodiments the reinforcing element 102 may comprise a mesh (such as a stent) having a generally tubular structure that surrounds a lumen extending between open longitudinal ends. The reinforcing element 102 may have a first end portion 102a, a second end portion 102b, and a length extending therebetween along the longitudinal axis L of the reinforcing element 102.

While the views provided in several of the figures provided herein show expandable devices laid flat for ease of explanation and understanding, the devices can be formed into a tubular shape. Also, as used herein, the term "longitudinal" can refer to a direction along an axis that extends through the lumen of the device while in a tubular configuration, and the term "circumferential" can refer to a direction along an axis that is orthogonal to the longitudinal axis and extends around the circumference of the device when in a tubular configuration.

According to some embodiments, for example as shown in FIGS. 4A and 4B, the mesh can comprise a plurality of struts 210 within a plurality of strut sections 202a-202d (referred to collectively as "strut sections 202"), a plurality of first spines 212 (labeled individually as 212a and 212b) and a plurality of second spines 214 (labeled individually as 214a, 214b, and 214c) extending substantially longitudinally across and between the strut sections 202, a plurality of first outer eyelets 205, a plurality of second outer eyelets 204, a plurality of opposing eyelets 203, and a plurality of junctions 230 and 232. The first and second spines 212 and 214 are collectively referred to herein as "spines 216." Only selected ones of the struts, spines, eyelets, and junctions have been labeled in FIG. 4B for ease of illustration. In some embodiments, all of the strut sections 202 and the spines 216 can extend along some or all of a circumference of the reinforcing element 102 when the reinforcing element 102 forms a tubular shape (i.e., its treatment shape).

In some embodiments, for example as shown in FIG. 4B, each end of one, some, or all of the struts 210 can be connected to a spine 216. For example, a first end of all of the struts 210 in in all of the strut sections 202 connects to a first spine 212 and a second end of all of the struts 210 in all of the strut sections 202 connect to a second spine 214. In some embodiments, a first end of one, some, or all of the struts 210 in one, some, or all of the strut sections 202 connects to a first spine 212 and a second end of one, some, or all of the struts 210 in one, some, or all of the strut sections 202 connect to a second spine 214. In some embodiments, the first and second ends of one, some, or all of the struts 210 in one, some, or all of the strut sections 202 connects to a first spine 212. In some embodiments, the first and second ends of one, some, or all of the struts 210 in one, some, or all of the strut sections 202 connect to a second spine 214. The struts 210 may connect to the first and/or second spines 212, 214 at a strut-eyelet junction 230 or at a strut junction 232 (only a few labeled). As depicted, the struts 210 can be arranged in a serpentine pattern where the struts 210 change longitudinal directions after crossing a spine. Some or all of the junctions can be formed at longitudinal ends of a strut section 202.

As previously mentioned, the mesh of the reinforcing element 102 may include first and second spines 212, 214 that extend longitudinally along the mesh. In some embodiments, all or a portion of one, some, or all of the first spines 212 can be parallel to all or a portion of one, some, or all of the second spines 214. In some embodiments, all or some of one, some, or all of the first spines 212 can be parallel to all or a portion of one, some, or all of the other first spines 212. In some embodiments, all or some of one, some, or all of the second spines 214 can be parallel to all or a portion of one, some, or all of the other second spines 214. In some embodiments, such as that shown in FIG. 4B, the first and second spines 212, 214 alternate around a circumference of the mesh. In some embodiments, at least one first spine 212 is directly radially adjacent at least one other first spine 212, and in some embodiments, at least one second spine 214 is directly radially adjacent at least one other second spine 214.

As shown in FIG. 4B, a first spine 212 may extend across less than all of the strut sections 202, and a second spine 214 may extend across all of the strut sections 202. The mesh may include an intermediate region 218 comprising opposing eyelets 203 and bridging portions 214c of the second spines 214. The first spines 212 may not extend into the intermediate region 218 and thus may form two circumferential sections 212a and 212b that are spaced apart along the longitudinal axis of the mesh. In some embodiments, one, some, or all of the first spines 212 may span only two strut sections 202. Within the intermediate region 218, a periphery of each of the opposing eyelets 203 and the bridging portions 214c of the second spines 212 may enclose a gap 206. The opposing longitudinal ends of the opposing eyelets 203 may be separated a distance $d_1$ across the gap 206. In some instances, one, some, or all of the first spines 212 extend between second outer eyelets 204 and the adjacent one of the opposing eyelets 203. The first and second longitudinal ends of one, some, or all of the second spines 214 may terminate at second outer eyelets 205.

Figure 5:
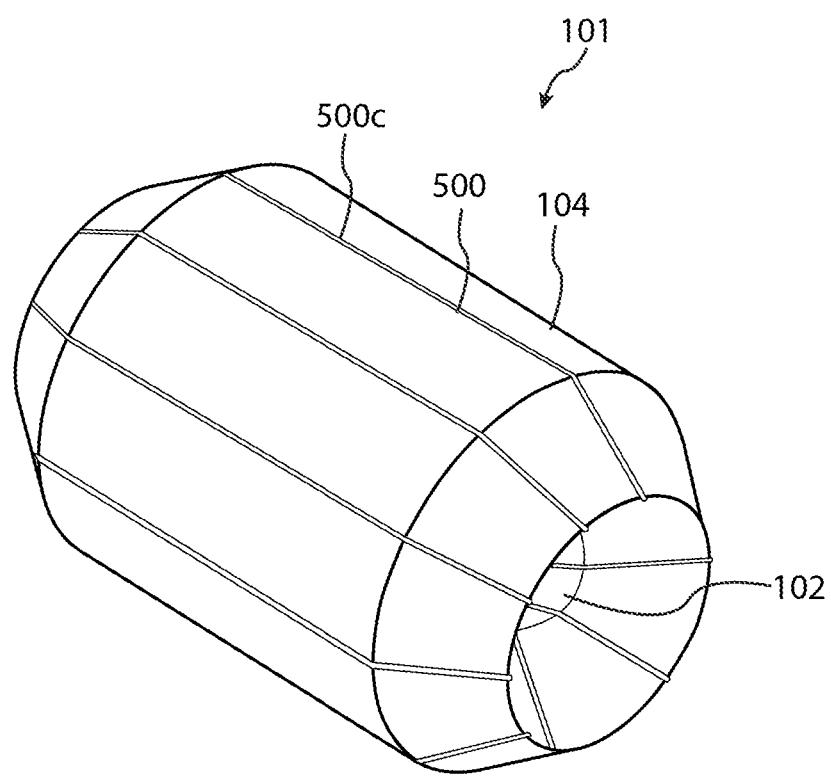
FIG. 5 is an isometric view of a treatment element of the present technology.
Figure 6A:
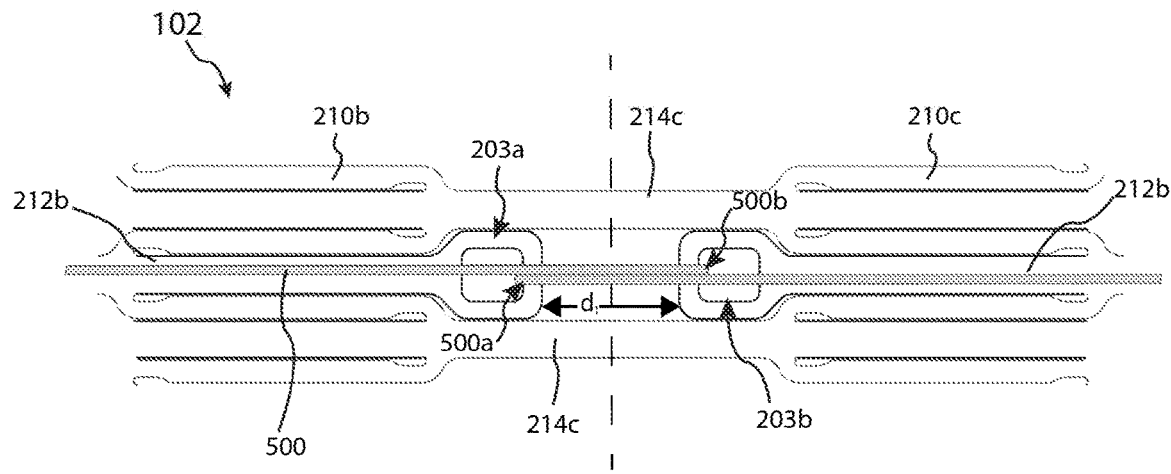
FIG. 6A is an enlarged, isolated view of a portion of the reinforcing element of FIGS. 4A and 4B while the reinforcing element is in a collapsed state.

FIG. 5 is an isolated view of one example of a treatment element 101, shown in an expanded configuration, where the treatment element 101 includes the reinforcing element 102 shown in FIGS. 4A and 4B. The reinforcing element 102 is shown schematically in FIG. 5 for ease of illustration. FIG. 6A is an enlarged view of a portion of the reinforcing element 102, depicted as positioned in a collapsed state within the lumen of the expandable element 104. With reference to FIGS. 5 and 6A, in some embodiments the reinforcing element 102 may be coupled to the expandable element 104 via one or more connectors 500. The connector 500 may comprise at least one of a strand, a suture, a wire, a thread, a tether, a fiber, a filament, or other suitable connecting member. Each connector 500 may have a first portion 500a coupled to the reinforcing element 102 at a first location along the reinforcing element 102, a second portion 500b coupled to the reinforcing element 102 at a second location along the reinforcing element 102, and an intermediate portion 500c (FIG. 5) extending between the first and second portions 500a and 500b. In some embodiments, the first location is an eyelet 203a of an opposing eyelet pair, and the second location is the other eyelet 203b of the opposing eyelet pair.

The intermediate portion 500c of the connector 500 may extend over a radially outer surface of the expandable element 104, as shown in FIG. 5. In some embodiments, all or a portion of the length of the intermediate portion 500c may extend substantially longitudinally along the expandable element 104. As shown in FIG. 5, in some embodiments a plurality of connectors 500 can be spaced apart along the radially outer surface of the expandable element 104. In some embodiments, each of such connectors 500 can be separately coupled to the reinforcing element 102 at separate or overlapping locations. For example, each connector 500 may be coupled to a separate eyelet or other structure of the reinforcing element 102, or two or more connectors 500 may be coupled to the same eyelet or other structure of the reinforcing element 102.

In some embodiments, such as that shown in FIGS. 4A-6B, the first location is positioned at a longitudinal location along the reinforcing element between the first end and the second location, and the connector extends from the second location past the first location to the first end, then inverts and extends along an outer surface of the expandable element to the second end of the reinforcing element, then inverts and extends along the reinforcing element towards the second end past the second location to the first location.

Figure 6B:
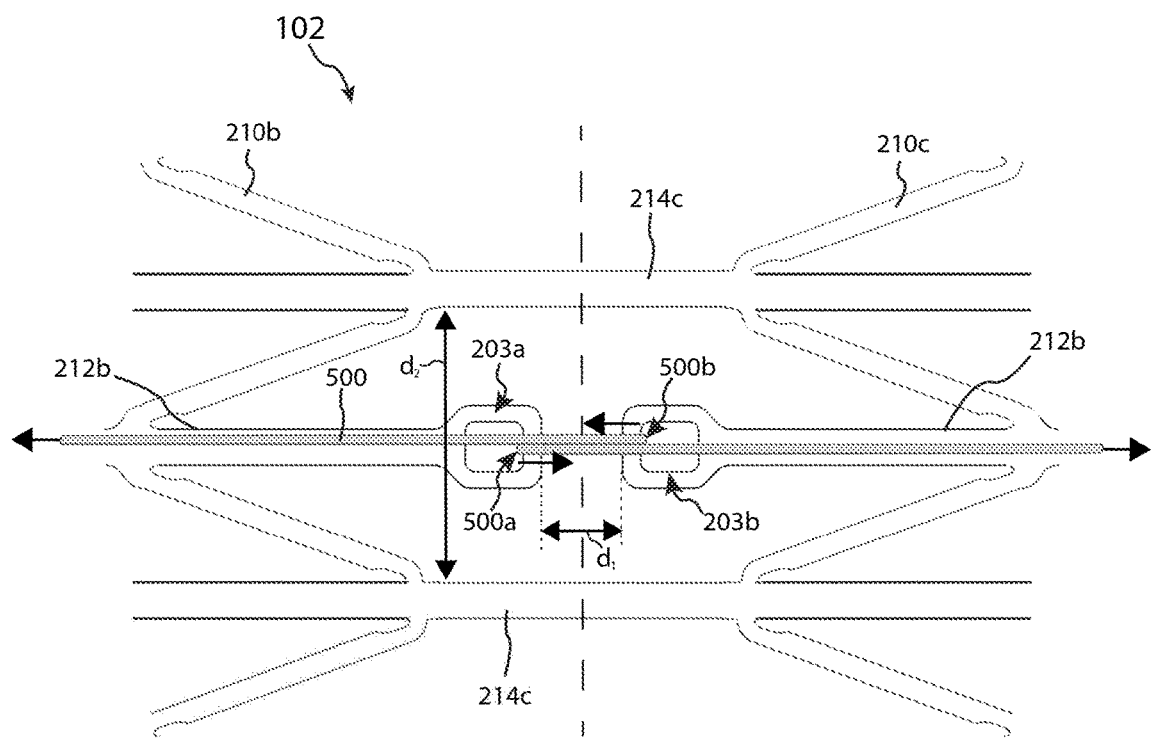
FIG. 6B is an enlarged, isolated view of the portion of the reinforcing element shown in FIG. 6A as the reinforcing element moves from the collapsed state of FIG. 6A to an expanded state.

In use, as the expandable element 104 is inflated, the outer wall of the expandable element 104 is pushed radially outwardly which pushes the intermediate portion 500c of the connector(s) 500 radially outwardly or radially away from the reinforcing element 102. As a result, the first portion 500a of the connector 500 pulls the corresponding eyelet (203a in FIG. 6B) in a first longitudinal direction and the second portion 500b of the connector 500 pulls the corresponding eyelet (203b in FIG. 6B) in a second longitudinal direction opposite the first longitudinal direction such that a distance $d_1$ between the opposing eyelets 203a and 203b decreases. During this time the first spines 212 are also being pulled longitudinally by their corresponding eyelet 203, which puts a stress at the junctions 230, 232, thereby causing the struts 210 to flex at their joints and angle away from the adjacent spines. As the struts 210 swing out from the spines, the struts 210 push radially adjacent spines away from one another, thereby increasing the distance $d_2$ between the spines (as shown in FIG. 6B) and increasing a diameter of the reinforcing element 102.

As the connectors 500 pull the opposing eyelets 203 in opposite directions, the circumferential sections 212a, 212b of the first spines 212 move longitudinally towards one another, thereby shortening a length of the mesh as measured between the second outer eyelets 204. The second spines 214, however, do not change in length. As such, the reinforcing element 102 has selective foreshortening along its length.

Passing a flexible connector through the eyelets makes the eyelets act as pulleys and thereby reduces the force required to effect expansion. Using the eyelets as pulleys additionally can be advantageous for increasing the length of connector that must be pulled in order to expand the reinforcing element 102, which can be advantageous to provide more flexibility in the interaction between the expandable element 104 and the reinforcing element 102.

In some instances, the reinforcing element 102 may include a travel limiting element that prevents the reinforcing element 102 from radially expanding beyond a predetermined diameter and/or from lengthening beyond a predetermined length. For example, the reinforcing element could be designed with stops or elements which interfere once the reinforcing element 102 has opened to an appropriate diameter. In the examples shown in FIGS. 4A-6B, the connector portions passed through the opposing eyelets limit radial expansion of the reinforcing element 102. When the opposing eyelets 203 are pulled together and bump into each other, the expansion limit has been reached.

In some embodiments, the second outer eyelets 204 can be used as fairleads to keep the individual connectors 500 oriented and spaced appropriately as they wrap around the expandable element 104. For example, a particular connector could pass through an eyelet at one end of the reinforcing element 102, then through the more distant opposing eyelet, then through the other opposing eyelet, and then through the second outer eyelet 204 at the opposite end of the reinforcing element 102. Additionally or alternatively, the connector 500 can make more than one loop through the two opposing eyelets 203, creating additional force when pulling the opposing eyelets 203 together and making it easier for the expandable element 104 to expand the reinforcing element 102. The example reinforcing element 102 shown in FIGS. 4A-6B also provides the benefit of not needing to foreshorten; as previously discussed, only select spines need to foreshorten in order to effect stent expansion. This can be helpful with manufacturing and bonding to adjacent catheter and expandable element 104 structures.

The treatment element 101 of the present technology provides several advantages over the prior art. For example, because the treatment element 101 and/or expandable element 104 has a perfusion lumen when expanded, the expandable element 104 can remain expanded at the treatment site for an extended period of time (i.e., a minute or more). As a result, the treatment elements of the present technology provide more effective dilation of the stenosed native valve and of the prosthetic stent-valve being delivered, thereby reducing the likelihood of perivalvular leakage or stent slippage. The extended expansion time also reduces the possibility of incomplete or non-circular stent expansion, which can lead to valve leakage and/or increased valve deterioration and early valve failure. Additionally, the treatment elements of the present technology enable the clinician to dilate the valve more slowly or leave the valve partially dilated for a period of time, which improves the final positioning of the prosthetic valve as it improves targeting of position and depth of the valve deployment.

To avoid acute ventricular overexpansion and provide meaningful blood flow to the systemic circulation, the perfusion lumen may have a cross-sectional area of about 0.5 cm² to about 0.8 cm². A perfusion lumen of this size in the convention devices faces several challenges. First, for a catheter having such a large fixed lumen, it would not be possible to introduce it through a percutaneous sheath. Secondly, such a large perfusion lumen running through the center of the balloon would also be likely to collapse under the high pressure of the balloon unless the perfusion lumen is highly reinforced.

When the expandable element 104 is deflated, the decreasing fluid pressure within the expandable element 104 will allow the outer wall of the expandable element 104 to decrease, thereby allowing the shoulders of the expandable element 104 to elongate and flatten as the reinforcing element 102 naturally resumes its elongated, low-profile state.

Figure 7:
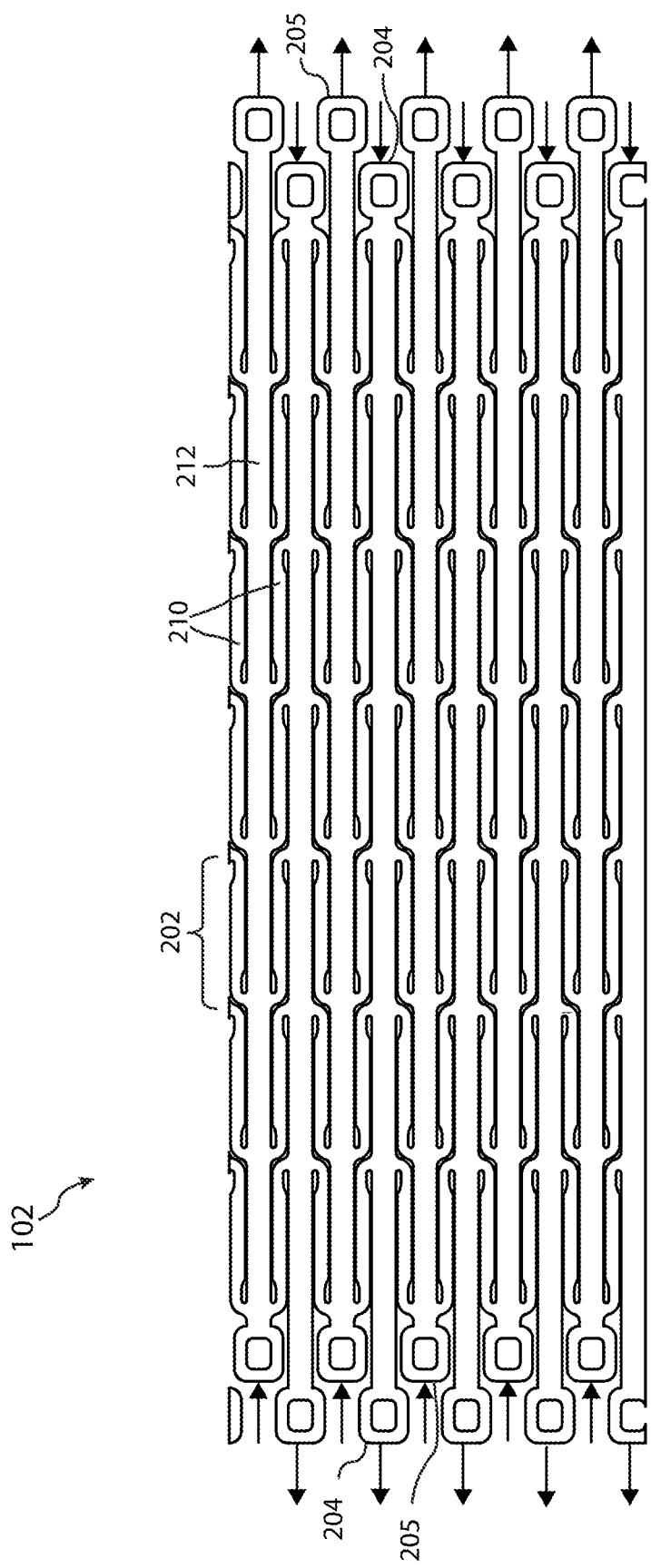
FIG. 7 is a top view of a reinforcing element of the present technology in a laid-flat configuration.

FIG. 7 depicts another example of a reinforcing element 102 for use with the treatment systems 100 of the present technology. The reinforcing element 102 of FIG. 7 is similar to the reinforcing element 102 of FIGS. 4A-6B, except: (a) the reinforcing element 102 of FIG. 7 does not have an intermediate region 216 with opposing eyelets 203, and (b) each of the spines has a first outer eyelet 204 at one end and a second outer eyelet 205 at the other end. To expand the reinforcing element 102, one or more connectors 500 may be threaded through or coupled to some or all of the first outer eyelets 205 such that the connector(s) extends from a first outer eyelet 205 at one end of the reinforcing element 102 and across the outer wall of the expandable element 104 to a first outer eyelet 205 at the other longitudinal end of the reinforcing element 102. As the expandable element 104 expands, the first outer eyelets are pulled longitudinally, thereby causing radial expansion of the reinforcing element 102. In contrast to the reinforcing element 102 of FIGS. 4A-6B, the reinforcing element 102 can change in its overall length as it expands. Additionally or alternatively, a compressive longitudinal force could be applied to the second outer eyelets 204 to radially expand the reinforcing element 102.

The reinforcing element 102 may be attached to the expandable element 104 at the ends of the reinforcing element 102. For example, the reinforcing element 102 may have fingers (not shown) extending from the ends of the reinforcing element 102 which are folded back against the outside of the reinforcing element 102. These fingers may be bonded to the ends of the expandable element 104, perhaps between the two tubes which form the expandable element. Alternatively, the fingers might have eyelets on both ends, and reinforcing connectors might be threaded back and forth between the eyelets at opposite ends over the outside of the expandable element. Therefore, the expandable element would be trapped between the stent on the inside, and the connectors on the outside. To avoid damaging the vessel wall or the heart valve (if it is being used for delivery of a valve), a second layer of expandable element material might be placed over these reinforcing connectors, or they might be bonded to the outside of the expandable element with adhesive or polymer.

As was the case with the reinforcing element 102 of FIGS. 4A-6B, the reinforcing element 102 of FIG. 7 may include a travel limiting element that prevents the reinforcing element 102 from radially expanding beyond a predetermined diameter and/or from lengthening beyond a predetermined length. For example, as depicted in FIG. 7, the reinforcing element 102 may include a flexible connector (e.g., a fiber, a suture, etc.) that loops through the first outer eyelets 705, thereby coupling the second outer eyelets 705 together. The connector in this case may have a length equivalent to the circumferential length of a desired expanded outer diameter of the reinforcing element 102. When the reinforcing element 102 expands to the preset diameter or length, the connector will prevent additional expansion. Additionally or alternatively, the first outer eyelets 205 could be coupled to first and/or second adjacent eyelets 204, 205 in such a fashion as to limit foreshortening, and thereby limit expansion of the outer diameter.

In some aspects of the technology, the expandable element 104 may be longer than the reinforcing element 102 and expansion of the reinforcing element 102 occurs via elongation of the reinforcing element 102. The reinforcing element 102 of FIG. 7, for example, could be used in such a manner. The expandable element 104 could be attached to first outer eyelets 205 of the reinforcing element 102. This attachment could be a direct connection by fusing the eyelets or other features with the wall or material comprising the expandable element 104 (such as a polymer), or again via connectors 500 that have been laced through the eyelets of the reinforcing element 102 and around the expandable element 104 to the eyelets at the other end of the reinforcing element 102.

Many of the embodiments disclosed herein utilize the force of the expandable element's expansion to expand the reinforcing element 102, even though expansion of the reinforcing element 102 reduces a volume of the expandable element 104 to some degree. For example, if the reinforcing element 102 were 30 mm long and had a relaxed diameter of 4 mm, and the reinforcing element 102 was then expanded to a diameter of 10 mm to create a perfusion lumen, then a volume of the reinforcing element 102 would increase by approximately 2.0 cm³. If the expandable element 104 surrounding the reinforcing element 102 is initially inflated with an interior diameter of 4 mm and the interior diameter expands to 10 mm, then a volume of the expandable element 104 would be reduced by that same 2 cc of volume. Therefore, in some embodiments it may be advantageous for the expandable element 104 to elongate as the reinforcing element 102 expands to create more volume than it is losing via the expansion of the reinforcing element 102, or the pressure of the expandable element 104 may keep the reinforcing element 102 deflated. For example, in an example where the expandable element 104 has an outer diameter of 26 mm and an interior diameter of 10 mm, elongation of the expandable element 104 by 8 mm would add approximately an additional 3.6 cm³ of volume. Therefore, if the reinforcing element 102, the expandable element 104, and the connector 500 arrangement is designed so that the expandable element 104 elongates by 8 mm as the reinforcing element 104 expands, then the system should preferentially cause the reinforcing element 104 to expand as the expandable element 104 is pressurized.

Figure 8A:
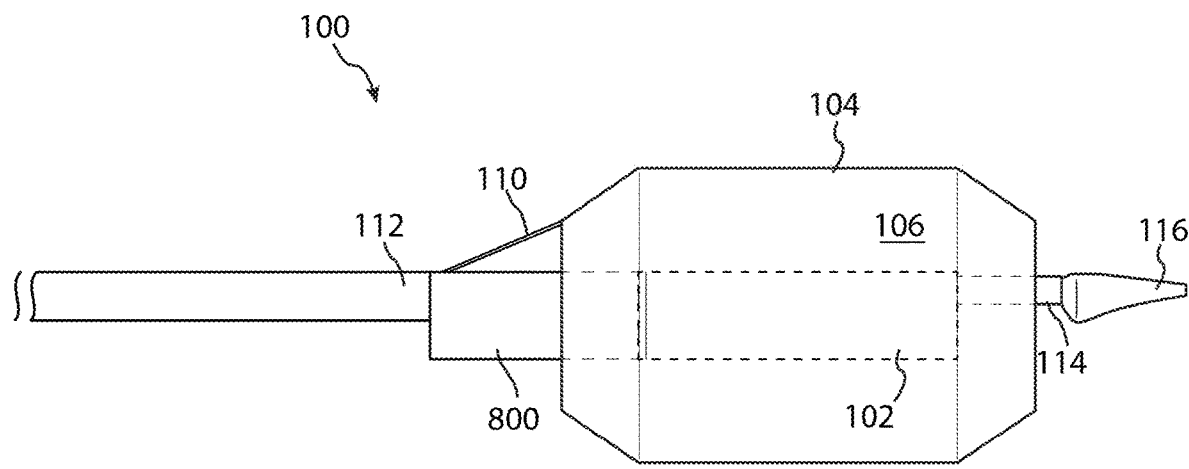
FIG. 8A is a side view of a distal portion of a treatment system of the present technology.
Figure 8B:
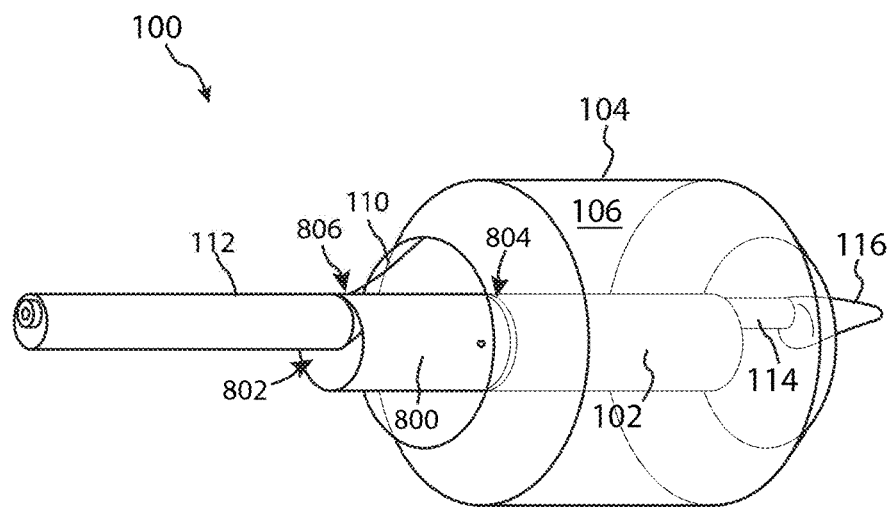
FIG. 8B is a rear isometric view of a distal portion of a treatment system of the present technology.

In some aspects of the technology, the perfusion lumen 108 may have a valve, such as a one-way valve, positioned at a location along its length. FIGS. 8A and 8B, for example, show an example treatment system 100 including a valve 800. In some embodiments, it may be especially beneficial to position the valve 800 at the proximal end of the expandable element 104, as shown in FIGS. 8A and 8B. In the example shown in FIG. 8A, the portion of the expandable element 104 surrounding the perfusion lumen 108 is extended proximally to form a short wind-sock valve which opens to permit blood to flow from the distal end of the catheter to the proximal end due to differential blood pressure. When the pressure proximally is higher than the pressure distally, the valve flattens against the elongated member 112 and impedes flow. Alternatively, if the expandable element 104 is being placed in such a way that the desired direction of flow is proximally to distally, the valve could be reversed and placed on the distal end of the expandable element 104 such that flow only proceeds distally.

The treatment system 100 may additionally or alternatively include other types of valves, such as an iris valve, a multi-leaflet valve, a duckbill valve, and others. Moreover, the valve 800 may be positioned at the distal end of the expandable element 104 or at any location along the length of the expandable element 104.

Figure 9A:
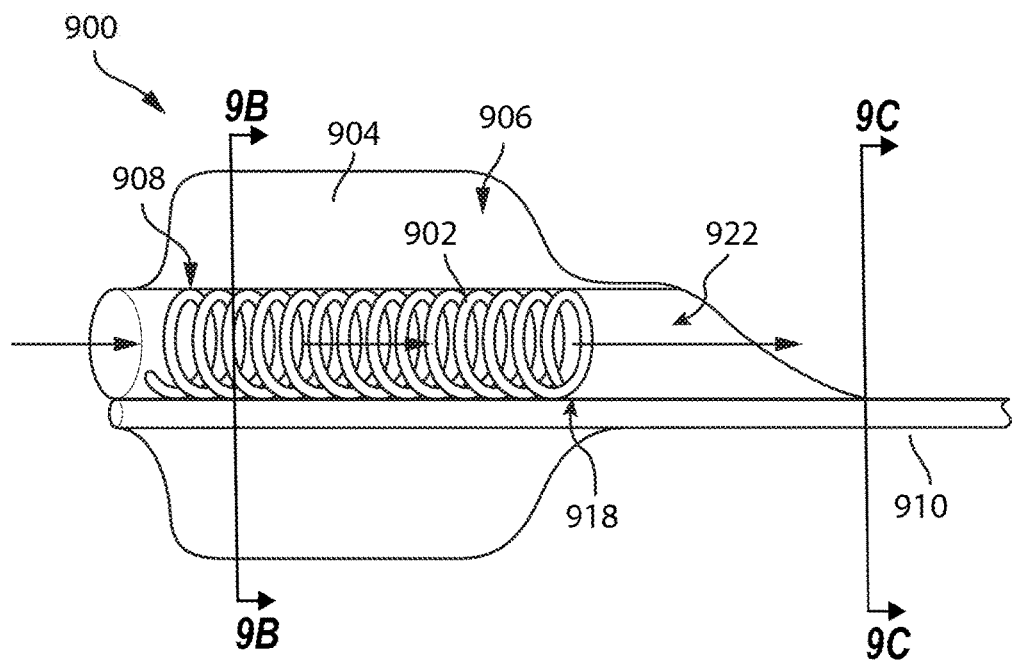
FIG. 9A is a schematic side view of a treatment system of the present technology, shown in an expanded configuration.
Figure 9B:
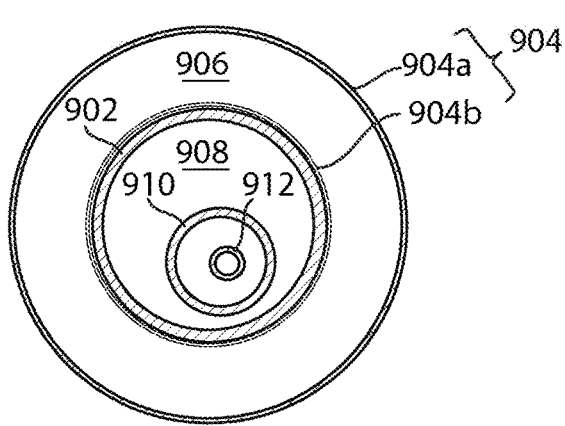
FIG. 9B is a cross-sectional end view taken along line 9B-9B in FIG. 9A.
Figure 9C:
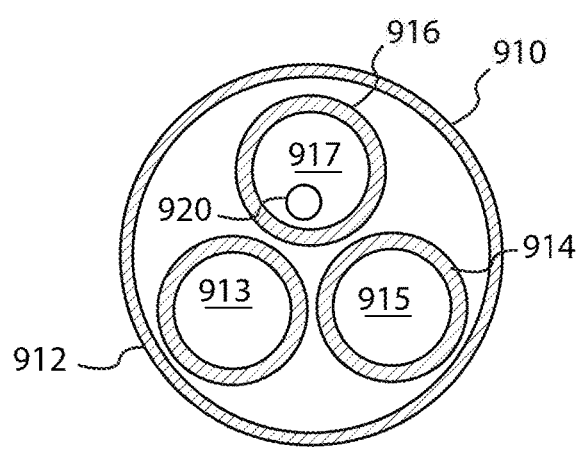
FIG. 9C is a cross-sectional end view taken along line 9C-9C in FIG. 9A.
Figure 10A:
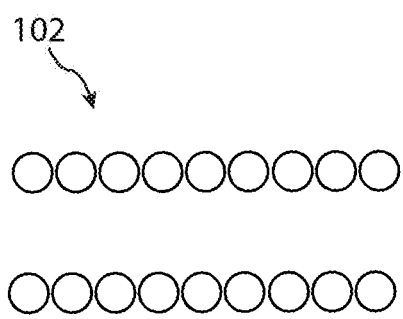
FIGS. 10A and 10B illustrate different reinforcing elements in accordance with the present technology.
Figure 10B:

FIGS. 9A-10B illustrate additional embodiments of a treatment system 100 in accordance with the present technology. FIG. 9A is a cross-sectional side view of the distal portion of the treatment system 100, FIG. 9B is a cross-sectional view taken along line 9B-9B, and FIG. 9C is a cross-sectional view taken along line 9C-9C. Referring to FIGS. 9A-9C together, the treatment system 100 may comprise an expandable element 904 (e.g., a balloon) carried by the distal portion of an elongated carrier shaft 910. The expandable element 904 and the distal portion of the carrier shaft 910 may be configured to be intravascularly and/or percutaneously positioned at a treatment site at or within a blood flow passage. The expandable element 904 may have a collapsed configuration (not shown) for delivery to the treatment site and an expanded configuration (as shown in FIG. 9A) in which the expandable element 904 defines a perfusion lumen 908 therethrough. As a result, when the expandable element 904 is expanded within the blood flow passage, the expandable element 904 allows blood flow through its lumen 908. A reinforcing element 902 can be disposed within the lumen 908 of the expandable element 904 and configured to maintain patency of the lumen 908.

The carrier shaft 910 may have at least three generally tubular elongated members 912, 914, and 916 extending at least a portion of its length therethrough. For example, the carrier shaft 910 may include: (a) a first elongated member 912 defining a first lumen 913 therethrough (such as a guidewire lumen) for atraumatic guidance of the catheter to the appropriate location; (b) a second elongated member 914 having defining a second lumen 915 (such as an inflation lumen) for inflation and deflation of the expandable element 904 with saline, contrast medium, or other appropriate fluid; and (c) a third elongated member 916 defining a third lumen 917 therethrough for delivery of a reinforcing element 902 (discussed in greater detail below) to the lumen 908 of the expandable element 904. In some embodiments, the three lumens 913, 915, 917 can be formed as lumens within a unitary carrier shaft 910, rather than as lumens defined by separate tubular members disposed within a common lumen of the carrier shaft 910. In some embodiments, the carrier shaft 910 may have more or fewer shafts or lumens (e.g., one shaft, two shafts, four shafts, five shafts, etc., and/or one lumen, two lumens, four lumens, five lumens, etc.).

The carrier shaft 910 may extend through the entire length of the perfusion lumen 908 and terminate distal to a distal end of the expandable element 904, and/or the reinforcing element 102. In some embodiments, the carrier shaft 910 may terminate at a location that is longitudinally aligned with or proximal of a distal end of the treatment element 101, the expandable element 104, and/or the reinforcing element 102. In other embodiments, the carrier shaft 910 may terminate at a more proximal location, with some or all of the elongated members 912, 914, 916 extending distally beyond a distal end of the carrier shaft 910.

The first elongated member 912 can extend substantially the entire length of the carrier shaft 910 and be configured to slidably receive a guidewire through the first lumen 913. The second elongated member 914 defining the second lumen 915 may extend between a proximal end portion (not shown) and a distal end portion that is fluidically coupled to the interior region 906 of the expandable element 904. For example, the carrier shaft 910 may have an opening in its sidewall to connect the second lumen 915 of the second elongated member 914 to the interior region 906 of the expandable element 904 (between the first and second tubes 904a, 904b). The second lumen 915 defined by the second elongated member 914 may be configured to deliver a fluid (e.g., saline, contrast solution) to the expandable element 904 to expand the expandable element 904. In some embodiments, second lumen 915 of the second elongated member 914 may be connected to the interior region 906 of the expandable element 904 via a separate tube.

The third elongated member 916 defining a third lumen 917 may extend between a proximal end portion (not shown) and a distal end portion that terminates adjacent a proximal end portion of the expandable element 904. In operation, a reinforcing element 902 (e.g., a wire) may be advanced through the third lumen 917, out of an opening 918 in the carrier shaft 910, and into the lumen 908 of the expandable element 904, as described in more detail below. For example, third lumen 917 may terminate at the opening 918 formed in a sidewall of the carrier shaft 910. The opening 918 may face towards the perfusion lumen 908 of the expandable element 904, at or near a proximal end portion of the expandable element 904. To facilitate advancement through the lumen 917, the reinforcing element 918 may be coupled to an elongated pusher element 920. In some embodiments, the pusher element 920 can be an elongated shaft or rod extending through the lumen 917 and coupled at its distal end to a proximal end of the reinforcing element 902, such that distally advancing the pusher element 920 causes the reinforcing element 902 to be distally advanced within the lumen 917.

In some embodiments, the expandable element 904 may be made from two extruded tubes, such as first and second tubes 904a and 904b, thereby defining an interior region 906. In such embodiments, the first tube 904a may be expanded to form the outer surface of the expandable element 904, and the second tube 904b may be used to form the inner lumen of the expandable element 904. The first and second tubes 904a and 904b may be welded together at their respective proximal and distal ends to form the expandable element 904. The first elongated member 912 may extend between these two expandable elements and into the interior region 906. The tubes of the expandable element 904 may be welded around the carrier shaft 910 at the proximal and distal ends of the expandable element 904. In some embodiments, the expandable element may may be formed of an inverted tube similar to that described above with respect to expandable element 204, with the first elongated member 912 extending into the interior region 906 defined by the expandable element.

The expandable element 904 may be made from one or more materials commonly used for balloons used in interventional procedures, such as polyethylene, polyolefin, polyurethane, nylon (polyamide), polyethylene terephthalate (PET or polyester), and/or other suitable polymers. The expandable element may also be a composite structure which may contain any polymer or polymers plus reinforcing fibers such as Kevlar, carbon-fiber, spectra or other high molecular weight polyethylenes, or other fibers in any orientation.

In some aspects of the technology, the perfusion lumen 908 may have a valve, such as a one-way valve, positioned at a location along its length. As shown in FIG. 9A, for example, the treatment system 900 including a valve 922. In some embodiments, it may be especially beneficial to position the valve 922 at the proximal end of the expandable element 904. In some embodiments, the portion of the expandable element 904 surrounding the perfusion lumen 908 extends proximally to form a short wind-sock valve which opens to permit blood to flow from the distal end of the treatment system 900 to the proximal end due to differential blood pressure. When the pressure proximally is higher than the pressure distally, the valve flattens against the carrier shaft 910 and impedes flow. Alternatively, if the expandable element 904 is being placed in such a way that the desired direction of flow is proximally to distally, the valve 922 could be reversed and placed on the distal end of the expandable element 904 such that flow only proceeds distally.

In some embodiments, the reinforcing element 902 may extend through at least a portion of the perfusion lumen 908. As shown in FIG. 9A, for example, the reinforcing element 902 can be a wire which is pre-formed to take the shape of a relatively closely wound coil, approximately the size of the perfusion lumen 908. Advancing the wire through the third lumen 917 of the third elongated member 916 causes the wire to be deployed into the perfusion lumen 908 where it resumes its coiled shape (shown in FIG. 9A) and reinforces the lumen 908. The wire may be distally advanced further into the perfusion lumen 908 until a distal end of the wire is at or near a distal portion of the expandable element 904. The wire may be round in cross-section (e.g., FIG. 10A), or generally square (e.g., FIG. 10B), or relatively ribbon-shaped, depending on the size and shape of the third lumen 917 and the number of coils which are desired to be deployed to reinforce the perfusion lumen 908. The wire can be metallic, polymeric, or any other suitable material. In some embodiments, the wire can be a shape-memory material (e.g., nitinol).

In some embodiments, to retrieve the system 900, the reinforcing element 902 (e.g., a coiled wire) may be proximally retracted into the lumen 917 of the third elongated member 916. Once the reinforcing element 902 has been retracted, the expandable element 904 may be deflated (e.g., by applying netative pressure via the second lumen 915 of the second elongated member 914), and the system 900 may be retracted into a catheter or otherwise removed from the treatment site.

In some embodiments, the reinforcing element could be a braid which is pre-formed to resume a relatively flat, close-wound tube when it is deployed into the perfusion lumen 908. Such a braided reinforcing element 902 can be attached at a distal end to the carrier shaft 910 and at a proximal end portion to a pusher element (not shown). When the pusher element is distally advanced relative to the carrier shaft 910, the reinforcing element 902 is foreshortened and urged to assume an expanded state. In this expanded state, the braid may provide an increased outward radial force to maintain patency of the perfusion lumen 908 and/or expand the expandable element 904. This may be advantageous in embodiments where it is preferred to expand the reinforcing element 902 at a separate time from expansion of the expandable element 904. For example, using such a configuration, the pusher element could be used to expand the reinforcing element before, concurrently with, or after expansion of the expandable element (e.g., via inflation through the second lumen 915).

In those embodiments for use in a valve replacement procedure (such as TAVR), the treatment system 100 may be configured for use with an expandable implantable valve apparatus (not shown). In some embodiments, the valve apparatus may be pre-loaded around an outer surface of the expandable element 104 such that the valve apparatus and the treatment element 101 are delivered to the native valve annulus together. When expanded at the treatment site, the treatment element 101 pushes radially outwardly against an inner surface of the valve apparatus, thereby forcing the valve apparatus to radially expand into apposition with the annular tissue. In some embodiments, the valve apparatus may already be expanded at the native valve annulus and the treatment element 101 may be delivered to an interior region of the valve apparatus and expanded to further expand or secure the valve apparatus at the annulus. In some embodiments the valve apparatus comprises only a laser-cut stent, and in some embodiments the valve apparatus comprises a laser-cut stent and a prosthetic heart valve configured for implantation at a native valve annulus.

CONCLUSION

Although many of the embodiments are described above with respect to systems, devices, and methods for treating cardiac disease, the technology is applicable to other applications and/or other approaches, such as pulmonary or cerebral applications. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 2A-10B.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

We claim:

1. A device for treating a blood flow passage of a patient, the device comprising:
    an expandable element configured to be positioned within the passage, the expandable element having a collapsed configuration and an expanded configuration in which the expandable element defines a lumen therethrough;
    a reinforcing element positioned within the lumen of the expandable element, the reinforcing element having a collapsed configuration and an expanded configuration in which the reinforcing element defines a lumen therethrough; and
    a connector having:
        a first portion coupled to the reinforcing element at a first location disposed within the lumen of the expandable element,
        a second portion coupled to the reinforcing element at a second location disposed within the lumen of the expandable element, and
        an intermediate portion between the first and second portions, wherein the intermediate portion extends over a radially outer surface of the expandable element,
    wherein the reinforcing element is coupled to the expandable element via the connector such that expansion of the expandable element causes the reinforcing element to radially expand, thereby creating a perfusion lumen through the device.

2. The device of claim 1, wherein the device is configured such that expansion of the expandable element while the device is positioned within the passage pulls the reinforcing element towards its expanded configuration, thereby allowing blood flow through the lumen of the reinforcing element and the lumen of the expandable element while the expandable element is in the expanded configuration.

3. The device of claim 1, wherein the expandable element causes radial expansion of the reinforcing element by applying a longitudinally oriented force to the reinforcing element.

4. The device of claim 3, wherein the force is longitudinally extensive.

5. The device of claim 3, wherein the force is longitudinally compressive.

6. The device of claim 1, wherein the reinforcing element is mechanically coupled to the expandable element during delivery of the device through a sheath to a treatment site.

7. The device of claim 1, wherein the expandable element is an inflatable element configured to expand when an inflation fluid is delivered to an interior region of the inflatable element.

8. The device of claim 1, wherein the expandable element extends between first and second longitudinal ends, and wherein the expandable element comprises a fold at the first longitudinal end and a seam at the second longitudinal end.

9. The device of claim 1, wherein the expandable element defines a single, continuous, annular inflation cavity.

10. The device of claim 1, wherein the expandable element is a balloon.

11. The device of claim 1, wherein the expandable element has a toroidal shape in the expanded configuration.

12. The device of claim 1, wherein the reinforcing element is a laser-cut stent.

13. The device of claim 1, wherein the intermediate portion of the connector extends substantially longitudinally along the radially outer surface of the expandable element.

14. The device of claim 1, wherein the connector comprises at least one of a strand, a suture, a wire, a thread, a tether, a fiber, or a filament.

15. The device of claim 1, wherein expansion of the expandable element causes the connector to pull the first and second locations toward one another, thereby causing the reinforcing element to radially expand.

16. A device for treating a blood flow passage of a patient, the device comprising:
    an expandable element configured to be positioned within the passage, the expandable element having a collapsed configuration and an expanded configuration in which the expandable element defines a lumen therethrough;
    a reinforcing element positioned within the lumen of the expandable element, the reinforcing element having a collapsed configuration and an expanded configuration in which the reinforcing element defines a lumen therethrough; and
    a connector having:
        a first portion coupled to the reinforcing element at a first location disposed within the lumen of the expandable element, wherein the first location comprises a first eyelet of the reinforcing element,
        a second portion coupled to the reinforcing element at a second location disposed within the lumen of the expandable element, wherein the second location comprises a second eyelet of the reinforcing element, and an intermediate portion between the first and second portions, wherein the intermediate portion extends over a radially outer surface of the expandable element, wherein the reinforcing element is coupled to the expandable element via the connector such that expansion of the expandable element causes the reinforcing element to radially expand, thereby creating a perfusion lumen through the device, and wherein a longitudinal distance between the first and second eyelets decreases in response to expansion of the expandable element.

17. The device of claim 1, further comprising a plurality of connectors, each having first and second portions coupled to the reinforcing element and an intermediate portion between the first and second portions, the intermediate portion extending over the radially outer surface of the expandable element.

18. The device of claim 1, further comprising a travel limiter configured to limit longitudinal elongation and/or compression of the reinforcing element in response to expansion of the expandable element.

19. The device of claim 18, wherein the travel limiter comprises one or more pairs of opposing eyelets coupled to one another via a flexible connector.

20. The device of claim 1, further comprising a valve coupled to the reinforcing element and/or the expandable element, wherein the valve is configured to control fluid flow through the lumen of the reinforcing element.

21. A device for treating cardiac or cardiovascular disease, the device comprising:
an expandable element comprising an outer wall and an inner wall, the outer and inner walls meeting at their respective longitudinal ends, wherein the expandable element has a collapsed configuration and an expanded configuration, and wherein the inner wall defines a lumen extending along a longitudinal axis of the expandable element;
a reinforcing element positioned within the lumen; and
a connector having:
a first portion coupled to the reinforcing element at a first location disposed within the lumen of the expandable element,
a second portion coupled to the reinforcing element at a second location disposed within the lumen of the expandable element, and
an intermediate portion between the first and second portions, wherein the intermediate portion extends over a radially outer surface of the expandable element,
wherein expansion of the expandable element from a collapsed configuration to an expanded configuration causes the reinforcing element to radially expand.

22. A system for treating a blood flow passage of a patient, the system comprising:
a treatment element comprising:
an expandable element comprising an outer wall and an inner wall, the outer and inner walls meeting at their respective longitudinal ends, wherein the expandable element has a collapsed configuration and an expanded configuration, and wherein the inner wall defines a lumen extending along a longitudinal axis of the expandable element, and
a reinforcing element positioned within the lumen,
a connector having:
a first portion coupled to the reinforcing element at a first location disposed within the lumen of the expandable element,
a second portion coupled to the reinforcing element at a second location disposed within the lumen of the expandable element, and
an intermediate portion between the first and second portions, wherein the intermediate portion extends over a radially outer surface of the expandable element,
wherein expansion of the expandable element from a collapsed configuration to an expanded configuration causes the reinforcing element to radially expand;
a first elongated member defining a lumen therethrough, the lumen in fluid communication with an interior region of the expandable element, wherein the first elongated member is configured to deliver a fluid to an interior region of the expandable element to expand the expandable element; and
a second elongated member, wherein a distal portion of the second elongated member is coupled to the reinforcing element.

23. The system claim 22, wherein the second elongated member defines a lumen extending therethrough, and wherein the lumen is configured to slidably receive a guidewire.

24. The system of claim 22, wherein only a portion of the reinforcing element is fixed to the second elongated member such that the reinforcing element can change in length while coupled to the second elongated member.

25. The system of claim 22, further comprising a third elongated member configured to receive the first elongated member and the second elongated member therethrough.

26. The system of claim 25, wherein the third elongated member terminates distally at a location proximal of the expandable element.

27. The device of claim 16, wherein the first and second eyelets are circumferentially aligned.

28. A device for treating a blood flow passage of a patient, the device comprising:
an expandable element configured to be positioned within the passage, the expandable element having a collapsed configuration and an expanded configuration in which the expandable element defines a lumen therethrough;
a reinforcing element positioned within the lumen of the expandable element, the reinforcing element having a collapsed configuration and an expanded configuration in which the reinforcing element defines a lumen therethrough; and
a connector having:
a first portion coupled to the reinforcing element at a first location disposed within the lumen of the expandable element;
a second portion coupled to the reinforcing element at a second location disposed within the lumen of the expandable element; and
an intermediate portion between the first and second portions, wherein the intermediate portion extends over a radially outer surface of the expandable element,
wherein the reinforcing element extends longitudinally between first and second ends, wherein the first location is positioned at a longitudinal location along the reinforcing element between the first end and the second location, wherein the connector extends from the second location past the first location to the first end, then inverts and extends along the radially outer surface of the expandable element to the second end of the reinforcing element, then inverts and extends along the reinforcing element towards the first end past the second location to the first location;

wherein the reinforcing element is coupled to the expandable element via the connector such that expansion of the expandable element causes the reinforcing element to radially expand, thereby creating a perfusion lumen through the device.

* * * * *